US009624160B2

(12) United States Patent
Schmidt et al.

(10) Patent No.: US 9,624,160 B2

(45) Date of Patent: Apr. 18, 2017

(54) REACTIVE IONIC LIQUIDS

(71) Applicant: BASF SE, Ludwigshafen (DE)

(72) Inventors: Michael Schmidt, Seeheim-Jugenheim (DE); Nikolai (Mykola) Ignatyev, Duisburg (DE); William-Robert Pitner, Frankfurt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/620,861

(22) Filed: Feb. 12, 2015

(65) Prior Publication Data

US 2015/0152045 A1 Jun. 4, 2015

Related U.S. Application Data

(63) Continuation of application No. 12/990,029, filed as application No. PCT/EP2009/002329 on Mar. 31, 2009, now Pat. No. 9,006,457.

(30) Foreign Application Priority Data

Apr. 29, 2008 (DE) ........................ 10 2008 021 271

(51) Int. Cl.

| | |
|---|---|
| ***C07C 229/12*** | (2006.01) |
| ***C07C 211/63*** | (2006.01) |
| ***C07C 219/04*** | (2006.01) |
| ***C07C 225/06*** | (2006.01) |
| ***C07C 309/06*** | (2006.01) |
| ***C07C 309/65*** | (2006.01) |
| ***C07F 9/28*** | (2006.01) |
| ***C07D 207/08*** | (2006.01) |
| ***C07D 211/14*** | (2006.01) |
| ***C07D 263/04*** | (2006.01) |
| ***C07D 295/037*** | (2006.01) |
| ***C07C 229/08*** | (2006.01) |
| ***C07C 255/25*** | (2006.01) |
| ***C07C 311/48*** | (2006.01) |
| ***C07C 317/04*** | (2006.01) |
| ***C07D 295/088*** | (2006.01) |
| ***C07D 295/108*** | (2006.01) |
| ***C07D 295/145*** | (2006.01) |
| ***C07F 9/54*** | (2006.01) |
| ***C07F 9/6568*** | (2006.01) |
| ***H01B 1/12*** | (2006.01) |
| ***H01M 10/052*** | (2010.01) |
| ***H01M 10/0569*** | (2010.01) |
| ***H01G 11/06*** | (2013.01) |
| ***H01G 11/58*** | (2013.01) |
| ***C07F 9/30*** | (2006.01) |
| ***H01G 11/60*** | (2013.01) |
| ***H01G 11/62*** | (2013.01) |

(Continued)

(52) U.S. Cl.

CPC .......... *C07C 229/12* (2013.01); *C07C 211/63* (2013.01); *C07C 219/04* (2013.01); *C07C 225/06* (2013.01); *C07C 229/08* (2013.01); *C07C 255/25* (2013.01); *C07C 309/06* (2013.01); *C07C 309/65* (2013.01); *C07C 311/48* (2013.01); *C07C 317/04* (2013.01); *C07D 207/08* (2013.01); *C07D 211/14* (2013.01); *C07D 263/04* (2013.01); *C07D 295/037* (2013.01); *C07D 295/088* (2013.01); *C07D 295/108* (2013.01); *C07D 295/145* (2013.01); *C07F 9/28* (2013.01); *C07F 9/301* (2013.01); *C07F 9/5428* (2013.01); *C07F 9/65688* (2013.01); *H01B 1/122* (2013.01); *H01G 11/06* (2013.01); *H01G 11/58* (2013.01); *H01G 11/60* (2013.01); *H01G 11/62* (2013.01); *H01G 11/64* (2013.01); *H01M 10/052* (2013.01); *H01M 10/0567* (2013.01); *H01M 10/0568* (2013.01); *H01M 10/0569* (2013.01); *H01M 10/0525* (2013.01); *Y02E 60/122* (2013.01); *Y02E 60/13* (2013.01)

(58) Field of Classification Search

None

See application file for complete search history.

(56) References Cited

U.S. PATENT DOCUMENTS

| | | |
|---|---|---|
| 3,723,512 A | 3/1973 | Niederprum et al. |
| 4,131,633 A | 12/1978 | Doorakian et al. |

(Continued)

FOREIGN PATENT DOCUMENTS

| | | |
|---|---|---|
| CN | 10121000 | 3/1991 |
| CN | 101085762 | 12/2007 |

(Continued)

OTHER PUBLICATIONS

Johan Jacquemin et al., "Prediction of Ionic Liguid Properties. I. Volumetric Properties as a Function of Temperature at 0.1 MPa", Journal of Chemical and Engineering Data, 53, 2008, pp. 716-726.

Wataru Ogihara et al., Effect of Cation Structure on the Electrochemical and Thermal Properties of Ion Conductive Polymers Obtained from Polymerizable Ionic Liquids, Electrochimica Acta, 51, 2006, pp. 2614-2619.

Lee et ai, "Ionic Liquids containing an ester group as potential electrolytes", Electrochem. Comm., 8, Feb. 15, 2006, 460-464.

Esgashira, M. et al., "Charge-discharge and high temperature reaction of LiCo02 in ionic liquid electrolytes based on cyano-substituted quarterly ammonium cation," Journal of Power Sources, 2006, vol. 160, pp. 1387-1390.

Galinski, M. et al., "Ionic Liquids as electrolytes," Electrochimica Acta, 2006, vol. 51, pp. 5567-5580.

(Continued)

*Primary Examiner* — Nyeemah A Grazier

(74) *Attorney, Agent, or Firm* — Oblon, McClelland, Maier & Neustadt, L.L.P.

(57) ABSTRACT

The invention relates to reactive ionic liquids containing organic cations with groups or substituents which are susceptible to electrochemical reduction and anions obtained from fluoroalkyl phosphates, fluoroalkyl phosphinates, fluoroalkyl phosphonates, acetates, triflates, imides, methides, borates, phosphates and/or aluminates, for use in electrochemical cells, such as lithium ion batteries and double-layer capacitors.

17 Claims, No Drawings

(51) Int. Cl.

| | |
|---|---|
| ***H01G 11/64*** | (2013.01) |
| ***H01M 10/0567*** | (2010.01) |
| ***H01M 10/0568*** | (2010.01) |
| *H01M 10/0525* | (2010.01) |

(56) References Cited

U.S. PATENT DOCUMENTS

| | | | |
|---|---|---|---|
| 7,479,353 | B2 | 1/2009 | Hollenkamp et al. |
| 8,148,533 | B2 | 4/2012 | Paonessa et al. |
| 8,173,305 | B2 | 5/2012 | Holzapfel et al. |
| 2005/0191559 | A1 | 9/2005 | Warner et al. |
| 2005/0196671 | A1 | 9/2005 | Paonessa et al. |
| 2006/0210876 | A1 | 9/2006 | Kuboki et al. |
| 2009/0036715 | A1 | 2/2009 | Chen et al. |
| 2009/0045373 | A1 | 2/2009 | Hammami et al. |
| 2012/0296096 | A1 | 11/2012 | Shinohara et al. |
| 2012/0309981 | A1 | 12/2012 | Ignatyev et al. |
| 2012/0309982 | A1 | 12/2012 | Shinohara et al. |
| 2013/0004860 | A1 | 1/2013 | Nishida et al. |
| 2013/0344399 | A1 | 12/2013 | Sutto |

FOREIGN PATENT DOCUMENTS

| | | | | |
|---|---|---|---|---|
| DE | 2609474 | | 9/1977 | |
| JP | 2004-6215 | A | 1/2004 | |
| JP | 2005-149982 | A | 6/2005 | |
| JP | 2005-251510 | A | 9/2005 | |
| JP | 2005-255843 | A | 9/2005 | |
| JP | 2006-206517 | | 8/2006 | |
| JP | 2007-161678 | | 6/2007 | |
| JP | 2007-280912 | A | 10/2007 | |
| WO | WO/01 25326 | | 4/2001 | |
| WO | WO 2004 035542 | | 4/2004 | |
| WO | WO 2005/027157 | A2 | 3/2005 | |
| WO | WO 2007 014722 | | 2/2007 | |
| WO | WO 2007147222 | A2 * | 12/2007 | ........... C07C 229/12 |

OTHER PUBLICATIONS

Hayashi, K. et al., "Electrolyte and secondary lithium battery which uses the electrolyte," Database Caplus Chemical Abstract Service, XP002531096.

Lee, J. S. et al., "Ionic liquids containing an ester group as potential electrolytes," Electrochemistry Communications, 2006, vol. 8, pp. 460-464.

Ma, K. et al., "Design Criteria for Ionic Liquid Crystalline Phases of Phosphonium Salts with Three Equivalent Long n-Alkyl Chains," Journal of Organic Chemistry, 2009, vol. 74, pp. 2088-2098.

Matsumoto, H. et al., "Room temperature ionic liquids based on small aliphatic ammonium cations and asymmetric amide anions," Chemical Communications, 2002, pp. 1726-1727, XP002312379.

Nquyen, D. Q. et al., "Synthesis and Characterization of Quarternary Ammonium-based Ionic Liquids Containing an Alkyl Carbonate Group," Bull. Korean Chem. Soc., 2007, vol. 28, No. 12, pp. 2299-2302.

Okoturo, O. O. et al., "Temperature dependence of viscosity for room temperature ionic liquids," Journal of Electroanalytical Chemistry, 2004, vol. 568, pp. 167-181.

Rockwool Mineralwolle, "Packaging and transport unit for panel-shaped insulating material elements," Thomson Innovation Record View, Publication Date: Feb. 8, 2007; English Abstract of WO-2007014722.

Solvent Innovation GMBH, "Functionalized ionic liquids and methods for the production thereof," Thomson Innovation Record View, Publication Date: Apr. 29, 2004, English Abstract of WO-2004035542.

Univ Shanghai Jiaotong, Thomson Innovation Record View, Publication Date: Dec. 12, 2007; English Abstract of CNI 01 085762.

Wu Jiaxing, "Magnetic Pump," Thomson Innovation Record View, Publication Date: Mar. 20, 1991; English Abstract of CNI 0121 00.

Yim, T. et al., "Synthesis and Properties of Pyrrolidinium and Piperidinium Bis(trifluoromethanesulfonyl) imide Ionic Liquids with Allyl Substituents," Bull. Korean Chem. Soc., 2007, vol. 28, No. 9, pp. 1567-1572.

Zhang, Q. et al., "Physicochemical Properties of Nitrile-Functionalized Ionic Liquids," J. Phys. Chem., 2007, vol. 111, pp. 2864-2872.

Zhang, Q. et al., "Synthesis of a New Kind of Ester Ionic Liquid," Chinese Journal of Organic Chemistry, 2007, vol. 27, No. 9, pp. 1167-1170.

Zhang, Q. et al., "Synthesis of Ionic Liquids Based on the N-methyl-N-allyl Morpholinium Cation," Chemical Journal of Chinese Universities, 2005, vol. 26, No. 2, pp. 340-342.

Egashira, M. et al., "Cyano-containing quaterly ammonium-based ionic liquid as a 'co-solvent' for lithium battery electrolyte," Journal of Power Sources, 2005, vol. 146, pp. 685-688.

Egashira, M. et al., "The preparation of quarterly ammonium-based ionic liquid containing a cyano group and its properties in a lithium battery electrolyte," Journal of Power Sources, 2004, vol. 138, pp. 240-244.

English Translation of JP-2006 206517, Aug. 10, 2006.

English Translation of JP-2007 161678, Jun. 28, 2007.

* cited by examiner

REACTIVE IONIC LIQUIDS

This application is a continuation application of U.S. Ser. No. 12/990,029 filed on Oct. 28, 2010 which is a 371 application of PCT/EP09/02329 filed on Mar. 31, 2009.

The invention relates to reactive ionic liquids containing organic cations with groups or substituents which are susceptible to electrochemical reduction and anions obtained from fluoroalkyl phosphates, fluoroalkyl phosphinates, fluoroalkyl phosphonates, acetates, triflates, methides, borates, phosphates and aluminates, for use in electrochemical cells, such as lithium ion batteries and double-layer capacitors.

Ionic liquids or liquid salts are ionic species which consist of an organic cation and a generally inorganic anion. They do not contain any neutral molecules and usually have melting points below 373 K.

“Reactive ionic liquids” are taken to mean ionic liquids which contain, on the organic cation, groups or substituents which are susceptible to electrochemical reduction, such as cyano groups, ester groups, carbonate groups or side chains with double bonds.

In recent years, ionic liquids have attracted ever increasing interest, and a large number of review articles have described unique properties of ionic liquids (“ILs” for short) and indicated various potential uses.

In particular, ionic liquids appear to be highly promising for use in energy-storage media, such as double-layer capacitors and batteries, with a particular focus on electric and hybrid vehicles.

Outstanding properties of ionic liquids include:

- virtually zero volatility and thus very high flash points
- a very large liquid range, in some cases above several 100 K
- very high polarity and thus generally very good solubility for inorganic and organic salts.

Whereas ionic liquids, such as, for example, ethylmethylimidazolium tetrafluoroborate ($EMIBF_4$), are already being employed commercially in double-layer capacitors (super- or ultracapacitors), use in batteries, in particular lithium ion batteries, continues to be difficult.

For battery applications, the following systems comprising ionic liquids have been characterised:

- ionic liquids in combination with electrolytes comprising an Li salt
- ionic liquids in combination with electrolytes comprising an Li salt plus additives The following ionic liquids have been used here:

- ionic liquids having $AlCl_4$ as anion (generation 0, very early work)
- ionic liquids having imidazolium-based cations and (per) fluorinated inorganic or organic anions (generation 1)
- ionic liquids having “non-imidazolium”-based cations and (per)fluorinated inorganic or organic anions (generation 2)

$AlCl_4$-based ionic liquids are extremely sensitive to hydrolysis and react with water with liberation of hydrochloric acid HCl. The development for battery systems has been stopped because of this. Imidazolium-based ILs exhibit inadequate reductive stability and are therefore not regarded as very promising for commercial application in high-energy batteries. Ionic liquids having inorganic anions, in particular $BF_4$, cause a significant reduction in capacitance, in particular in the first charge/discharge cycle. The ionic liquids which currently appear to be the most suitable for Li ion batteries use N,N-dialkylpyrrolidinium in combination with bis(trifluoromethyl)imides (see, for example, JP 2006-260952).

However, even these ionic liquids still cause a significant drop in the power densities of lithium ion batteries.

The reason for this is, in particular, the high viscosity of electrochemically stable ionic liquids. This results in significantly lower lithium ion conductivity of the IL-based electrolyte compared with standard electrolyte systems with no ionic liquids (O. Borodin et al., J. of Physical Chemistry B, 2006, 110 (34), pp. 16879-16886). Accordingly, lithium ion batteries comprising IL-based electrolytes still today exhibit a significantly lower power density and charge-carrying capacity compared with lithium ion batteries comprising standard electrolytes.

The latter in particular must be regarded as very critical for applications in electric and hybrid vehicles and prevents—in spite of an increase in safety—the use of IL-based electrolytes.

Lee et al. (Electrochem. Comm. 8 (2006) 460) have been able to show that the use of imidazolium-based ILs having ester ligands on the nitrogen in battery electrolytes results in an improvement in the lithium conductivity and diffusion coefficient of Li ions.

However, these imidazolium-based ionic liquids are not sufficiently electrochemically stable.

The object of the present invention was therefore to develop ionic liquids which have high thermal stability, very good oxidation stability and low corrosiveness, and have anions which have been synthesised inexpensively, and do not have the above-mentioned disadvantages.

The present object is achieved by ionic liquids of the general formula I $$K^+A^- \quad (I)$$

in which:

$K^+$ denotes a cation, preferably reduction-stable, selected from the group of the general formulae II to IX $NR_3$—R5 $PR_3$—R5

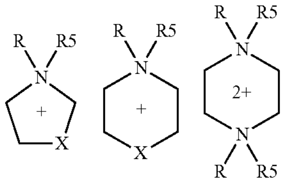

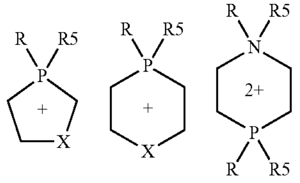

where

X denotes $CH_2$, O, S or NR'

R' denotes —$(CH_2)_n$—CN, $C_1$- to $C_{16}$-alkyl, preferably methyl, ethyl, propyl, H R denotes H, $C_1$- to $C_{16}$-alkyl, preferably methyl, ethyl, propyl R5 denotes —$(CH_2)_n$—O—C(O)—R, —$(CH_2)_n$—C(O)—OR, —$(CH_2)_n$—O—C(O)—OR, —$(CH_2)_n$—HC═CH—R or —$(CH_2)$, —CN, where individual $CH_2$ groups are replaced by O, S or NR, where n=1 to 8, and $A^-$ denotes an anion selected from the group $[F_yP(C_mF_{2m+1})_{6-y}]^-$ $(C_mF_{2m+1})_2P(O)O)^-$ $C_mF_{2m+1}P(O)O_2^{2-}$
$O—C(O)—C_mF_{2m+1}$
$O—S(O)_2—C_mF_{2m+1}$
$N(C(O)—C_mF_{2m+1})_2$
$N(S(O)_2—C_mF_{2m+1})_2$
$N(C(O)—C_mF_{2m+1})(S(O)_2—C_mF_{2m+1})$
$N(C(O)—C_mF_{2m+1})(C(O)F)$
$N(S(O)_2—C_mF_{2m+1})(S(O)_2F)$
$N(S(O)_2F)_2$
$C(C(O)—C_mF_{2m+})_3$
$C(S(O)_2—C_mF_{2m+1})_3$

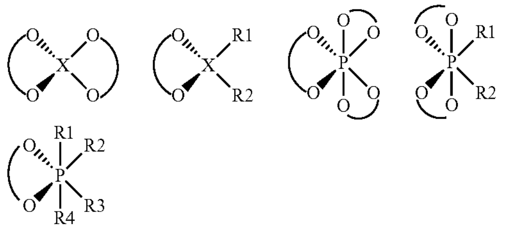

where y=1, 2, 3, 4 or 5, and m=1 to 8, preferably 1 to 4, where some of the $CF_2$ groups may be replaced by O, $S(O)_2$, NR or $CH_2$, and where

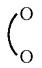

denotes a 1,2- or 1,3-diol, a 1,2- or 1,3-dicarboxylic acid or a 1,2- or 1,3-hydroxycarboxylic acid X denotes B or Al R1 to R4 denote halogen, in particular F, and/or a fluorinated or non-fluorinated alkoxy or carboxyl radical.

Compared with conventional ionic liquids, the reactive ionic liquids according to the invention are distinguished by the fact that they contain, on the organic cation, groups/substituents or side chains which are susceptible to electrochemical reduction. These are, in particular, cyano groups —CN ester groups —R—C(O)—OR or —R—O—C(O)—R carbonate functions —R—O—C(O)—OR double bonds in the side chains —R—CH═CH—R Surprisingly, the reactive ionic liquid's according to the invention form a passivating cover layer at potentials between about 2 V and 0.9 V against $Li/Li^+$ significantly sooner than ethylene carbonate (0.7 to 0.8 V against $Li/Li^+$). This cover layer is electronically passivating, but permeable to lithium ions. A further advantage consists in the excellent oxidation stability of >5 V against $Li/Li^+$. In contrast to many other additives employed at present, some of which are highly toxic (for example propane sultone), the reactive ionic liquids according to the invention are non-volatile and have no measurable vapour pressure.

The cations $K^+$ of the ionic liquids according to the invention are preferably cations selected from the general formula IV

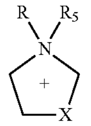

where

X denotes $CH_2$, O, S or NR'

R' denotes $—(CH_2)_n—CN$, methyl, ethyl, propyl, butyl, H

R denotes H, methyl, ethyl, propyl, butyl $R_5$ denotes $—(CH_2)_n—O—C(O)—R$, $—(CH_2)_n—C(O)—OR$, $—(CH_2)_n—O—C(O)—OR$, $—(CH_2)_n—HC═CH—R$ or $—(CH_2)_n—CN$, where individual $CH_2$ groups may be replaced by O, S or NR, where n=1 to 8.

The anions $A^-$ of the ionic liquids according to the invention are preferably the following anions: $[F_2P(C_2F_5)_4]^-$, $[F_3P(C_2F_5)_3]^-$, $[F_4P(C_2F_5)_2]^-$, $[F_2P(C_3F_7)_4]^-$, $[F_3P(C_3F_7)_3]^-$, $[F_4P(C_3F_7)_2]^-$, $[F_2P(C_4F_9)_4]^-$, $[F_3P(C_4F_9)_3]^-$, $[F_4P(C_4F_9)_2]^-$, perfluoroalkylcarboxylate, perfluoroalkylsulfonate, bis(perfluoroalkylsulfonyl)imide, (perfluoroalkylsulfonyl)(perfluoroalkylcarboxyl)imide, tris(perfluoroalkylsulfonyl)methide, particularly preferably trifluoroacetate, trifluoromethanesulfonate (triflate), bis(trifluoromethylsulfonyl)imide and tris(trifluoromethylsulfonyl)methide.

Preference is also given to spiro-oxo borates and spiro-oxo phosphates, particularly preferably spiro-oxo borates.

The invention furthermore relates to an electrolyte comprising at least one conductive salt, an aprotic solvent or solvent mixture, at least one ionic liquid of the above-mentioned formula I according to the invention, and optionally further additives.

In a preferred embodiment (for example on use of the electrolyte in lithium or lithium ion batteries), the conductive salt is a lithium conductive salt, such as $LiPF_6$, $LiN(SO_2CF_3)_2$, $LiN(SO_2C_2F_5)_2$, $LiF_3P(C_2F_5)_3$, $LiF_3P(C_4F_9)_3$, $LiB(C_2O_4)_2$ or $LiF_2B(C_2O_4)_2$.

In a further preferred embodiment (for example on use of the electrolyte in double-layer capacitors or supercapacitors), the conductive salt is a compound from the group $N(C_2H_5)_4BF_4N(C_2H_5)_4PF_6$, $N(C_2H_5)_3(CH_3)\ BF_4$, $N(C_2H_5)_3(CH_3)PF_6$, $N(C_2H_5)_4N(SO_2CF_3)_2$, $N(C_2H_5)_3(CH_3)N(SO_2CF_3)_2$, $N(C_2H_5)_4F_3P(C_2F_5)_3$, $N(C_2H_5)_3(CH_3)F_3P(C_2F_5)_3$.

The aprotic solvent of the electrolyte preferably consists of organic open-chain or cyclic carbonates, carboxylic acid esters, nitriles, ethers or lactones or a mixture thereof. Nitriles, in particular acetonitrile, are preferably employed as solvent in double-layer capacitors.

The present invention furthermore relates to a process for the preparation of ionic liquids of the formula I:

Preparation of heterocyclic cations $K^+$ containing alkyl-, carboxylate-, carbonate- or cyano-containing side chains according to Claim 1 as onium chlorides or bromides from the corresponding amines, phosphines, halocarboxylates, halocarbonates, haloalkyl-nitriles or alkyl halides by conventional wet-chemical methods, Reaction of these cationic onium chlorides or bromides with the corresponding anionic potassium and/or sodium fluoroalkylphosphates or potassium and/or sodium bis(fluoroalkyl)phosphinates or potassium and/or sodium fluoroalkylphosphonates or fluoroalkylphosphoric acids or bis(fluoroalkyl)phosphinic acids or fluoroalkylphosphonic acids or alkyl, in particular methyl, bis(fluoroalkyl) phosphinates or lithium imides or methides or trifluoromethanesulfonic acid or potassium or lithium trifluoroacetates or triflates or alkyl triflates or trimethylsilyl triflates or trifluoromethanesulfonic anhydride or trifluoroacetic anhydride or lithium or potassium borates, phosphates or aluminates in an aqueous and/or alcoholic medium or an organic solvent or without a solvent.

The preparation of the cations is known to the person skilled in the art and can be carried out by processes as described, for example, in P. Wasserscheid and T. Welton (Eds.) "Ionic Liquids in Synthesis", Wiley—VCH, 2003, pp. 7-40 in general or for imidazolium cations in N. Gathergood, P. J. Scammells, *Aust. J. Chem,* 55 (2002), No. 9, pp. 557-560; E. Alcalde, M. Gisbert, L. Perez-Garcia, *Heterocycles,* 43 (1996), No. 3, pp. 567-580; Z. Fei, D. Zhao, T. J. Geldbach, R. Scopelliti, P. J. Dyson, *Chem. Europ. J.,* 10 (2004), No. 19, pp. 4886-4893; D. Liu, Ji. Gui, X. Zhu, L. Song, Z. Sun, *Synth. Commun.,* 37 (2007), No. 5, pp. 759-765; Ya. Peng, F. Yi, G. Song, Yi. Zhang, *Monatsh. Chem.,* 136 (2005), No. 10, pp. 1751-1755; J. F. Dubreuil, J. P. Bazureau, *Tetrahedron Lett.,* 41 (2000), No. 38, pp. 7351-7356; S.-K. Fu, Sh.-T. Liu, *Synth. Commun.,* 36 (2006), No. 14, pp. 2059-2067; M. Yoshizawa, A. Narita, H. Ohno, *Aust. J. Chem.;* 57 (2004), No. 2, pp. 139-144; A. Narita, W. Shibayama, H. Ohno, *J. Mater. Chem.,* 16 (2006), No. 15, pp. 1475-1482; T. Mizumo, E. Marwanta, N. Matsumi, H. Ohno, *Chem. Lett.,* 33 (2004), No. 10, pp. 1360-1361; D. Zhao, Zh. Fei, T. J. Geldbach, R. Scopelliti, G. Laurenczy, P. J. Dyson, *Hel. Chim. Acta.,* 88 (2005), No. 3, pp. 665-675; A. Horvath, *Synthesis,* 1994, pp. 102-106; or for pyrrolidinium cations in L. Horner, A. Mentrup, *Justus Liebigs Ann. Chem.* 646 (1961), pp. 49-64; Bates et al., *J. Chem. Soc.* 1956, pp. 388-395, v. Braun *Chem. Ber.* 70 (1937), p. 983; Z. Dega-Szafran, R. Przybylak, *J. Mol. Struct.,* 436 (1997), No. 1, pp. 107-122; or for piperidinium cations in Walther et al., *Chem. Ber.,* 89 (1956), pp. 60-65; or for morpholinium cations in Gresham et al., *J. Am. Chem. Soc.,* 73 (1951), pp. 3168-3171; D. Le Berre, *Bull. Soc. Chim. Fr.,* 1973, pp. 2404-2407; O. A. Kazantsev, Kazakov, K. V. Shirshin, S. M. Danov, Russ. *J. Org. Chem.,* 36 (2000), No. 3, pp. 343-349; or for piperazinium cations in Z. Dega-Szafran, M. Jaskolski, I. Kurzyca, P. Barczynski, M. Szafran, *J. Mol. Struct.,* 614 (2002), No. 1-3, pp. 23-32.

The anions according to the invention are oxidation-stable, as can be seen from Tables 1.1 to 1.3.

TABLE 1.1

Electrochemical stability of reactive ionic liquids having a tris(pentafluoroethyl)trifluorophosphate anion (FAP anion) and a bis(pentafluoroethyl)phos-phinate anion, $(C_2F_5)_2P(O)O^-$, compared with similar ionic liquids having triflate and tetrafluoroborate anions

| Reactive ionic liquid | $E_{(ox)}$, V | $E_{(red)}$, V | Electrochem. window |
|---|---|---|---|
| 1-Ethyl-3-methyl-imidazolium FAP | 3.9 | −2.5 | 6.4 |
| 1-Ethyl-3-methyl-imidazolium $(C_2F_5)_2P(O)O^-$ | 3.6 | −2.6 | 6.2 |
| 1-Ethyl-3-methyl-imidazolium triflate | 2.8 | −2.5 | 5.3 |
| 1-Ethyl-3-methylimidazolium $BF_4^-$ | 2.6 | −2.6 | 5.2 |

TABLE 1.2

Electrochemical stability of reactive ionic liquids having a bis(trifluoromethylsulfonyl)imide anion and a triflate anion compared with the ionic liquid having a tetrafluoroborate anion

| Reactive ionic liquid | $E_{(OX)}$, V | $E_{(red)}$, V | Electrochem. window |
|---|---|---|---|
| 1-Butyl-1-methylpyrrolidinium bis(trifluoromethylsulfonyl)imide | −3.5 | −3.3 | 6.8 |
| Trihexyl(tetradecyl)phosphonium bis(trifluoromethylsulfonyl)imide | | −3.4 | 6.5 |
| 1-Hexyl-3-methylimidazolium bis(trifluoromethylsulfonyl)imide | 3.7 | −2.6 | 6.3 |
| 1-Ethyl-3-methylimidazolium triflate | 2.8 | −2.5 | 5.3 |
| 1-Ethyl-3-methylimidazolium $BF_4^-$ | 2.6 | −2.6 | 5.2 |

TABLE 1.3

Electrochemical stability of ionic liquids having borate, phosphate and aluminate anions

| | $E_{(ox)}$, vs. Li/Li$^+$ |
|---|---|
| 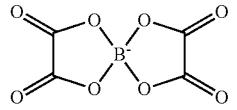 [SMILES: O=C1O[B-]2(OC1=O)OC(=O)C(=O)O2] Bisoxalatoborate (BOB) | 4.7-4.8 V |
| 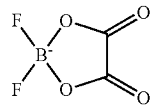 Difluorooxalatobotate (DFOB) | 4.8-5.0 V |
| 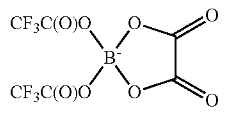 Di(trifluoroacetato)oxalatoborate (D(Ac)OB) | 4.8-5.0 V |
| 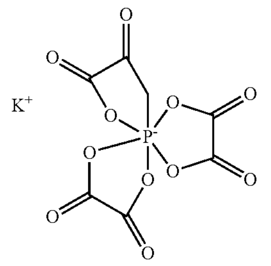 [SMILES: [K+] ; O=C1C[P-]23(OC1=O)(OC(=O)C(=O)O2)OC(=O)C(=O)O3] Potassium trisoxalatophosphate (KTOP) | 4.7-4.8 V |
| 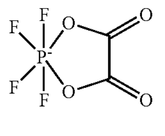 Tetrafluorooxalatophosphate (TFOP) | 4.8-5.0 V |

TABLE 1.3-continued

Electrochemical stability of ionic liquids having borate, phosphate and aluminate anions

| | $E_{(ox)}$, vs. Li/Li$^+$ |
|---|---|
| 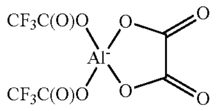<br>Di(triflouroacetato)oxalatoaluminate<br>(D(Ac)OAl) | >5 V |

The fluoroalkylphosphate-based reactive ionic liquids are prepared by reaction of the corresponding cationic onium chlorides or onium bromides with the corresponding potassium or sodium fluoroalkylphosphates or fluoroalkylphosphoric add (HFAP) in an aqueous medium.

The bis(fluoroalkyl)phosphinate-based ionic liquids are prepared by three different methods:

- preparation of these ionic liquids by means of phosphinic acid (see Example 5.1
- preparation of these ionic liquids via the corresponding potassium salts (such as potassium fluoroalkylphosphinate) (see Example 5.2)
- preparation of these ionic liquids via the corresponding alkyl bis(fluoroalkyl)phosphinates, preferably methyl phosphinates (see Example 5.3).

The preparation of the bis(fluoroalkyl)phosphinate-based ionic liquids via phosphinic acid and methyl phosphinates is preferred here.

The imide- and methide-based ionic liquids are prepared by reaction of the corresponding, cationic onium chlorides or onium bromides with the corresponding lithium salts in an aqueous medium.

The trifluoroacetate- and triflate-based ionic liquids are prepared by three different methods:

- preparation of the triflate-based ionic liquids by means of triflic acid (see Example 5.1
- preparation of the ionic liquids via the corresponding potassium or lithium trifluoroacetates or triflates (see Example 5.2)
- preparation of the ionic liquids via the corresponding methyl triflates, trimethylsilyl triflates, triflic anhydrides or trifluoroacetic anhydrides (see Example 5.3).

The preparation of the trifluoroacetate- and triflate-based ionic liquids via the triflic acid or trifluoroacetic acid and/or methyl or ethyl triflate or trifluoroacetate or trimethylsilyl triflate, triflic anhydride or trifluoroacetic anhydride method is preferred here.

The borate-, phosphate- or aluminate-based reactive ionic liquids are prepared by reaction of the corresponding, cationic onium chlorides or onium bromides with the corresponding anionic potassium or lithium borates, phosphates or aluminates in an aqueous or organic medium.

The reaction of the cations according to the invention with the anions to give the end product can be carried out at temperatures of 0 to 150° C., preferably at 0 to 50° C. and in particular at room temperature.

Suitable solvents or solvent mixtures are water or deionised water, alcohols, dioxane, acetonitrile and acetone. The alcohol employed is preferably methanol or isopropanol. In the case of the use of methyl phosphinates, a solvent is usually not needed.

The present invention furthermore relates to an electrochemical and/or electro-optical device containing at least one electrolyte which comprises at least one ionic liquid of the general formula I. The device can preferably be a solar cell, a lithium or lithium ion battery, a double-layer capacitor or supercapacitor, a lithium capacitor, a light-emitting device, an electrochemical sensor and/or a biosensor.

The present invention furthermore relates to the use of the said reactive ionic liquids of the general formula I as conductive salt or additive in electrolytes for electrochemical or electro-optical cells.

In a further preferred embodiment, the reactive ionic liquids according to the invention are used as conductive salt or additive in electrolytes for batteries, secondary lithium batteries, double-layer capacitors and supercapacitors or lithium capacitors.

The present invention furthermore relates to the use of the electrolytes according to the invention in electrochemical and/or electro-optical devices. These devices are preferably lithium or lithium ion batteries, double-layer capacitors, supercapacitors or lithium capacitors.

The following examples are intended to illustrate the present invention. However, they should in no way be regarded as limiting. All compounds or components which can be used in the compositions are either known and commercially available or can be synthesised by known methods. The temperatures indicated in the examples are always in ° C. It furthermore goes without saying that, both in the description and in the examples, the added amounts of the components in the compositions always add up to a total of 100%. Percentage data given should always be regarded in the given context. However, they usually always relate to the weight of the part amount or total amount indicated.

EXAMPLES

Preparation of the Cations

Example 1

Preparation of Heterocyclic Cations Containing Allyl Side Chains

General Procedure 1.1 mol of an allyl chloride are added dropwise to 1 mol of the corresponding amine or phosphine. It must be ensured here that the temperature is held at between 30 and 35° C. The reaction mixture is then stirred at 40° C. to 50° C. for 3 h to 48 h (in the case of the formation of solid products, the reaction mixture is diluted with dichloromethane or acetonitrile), and the excess allyl chloride and solvent are then distilled off in vacuo ($2 \cdot 10^{-3}$ mbar). The product yield is virtually quantitative.

TABLE 1

| Amine/phosphine employed | Allyl chloride employed | Product |
|---|---|---|
| $N(C_2H_5)_3$ | $Cl—CH_2—CH═CH_2$ | $[N(C_2H_5)_3(CH_2—CH═CH_2)]Cl$ |
| $N(CH_3)(C_2H_5)_2$ | $Cl—CH_2—CH═CH_2$ | $[N(CH_3)(C_2H_5)_3(CH_2—CH═CH_2)]Cl$ |
| $P(C_4H_9)_3$ | $Cl—CH_2—CH═CH_2$ | $[P(C_4H_9)_3(CH_2—CH═CH_2)]Cl$ |
| 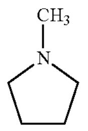 | $Cl—CH_2—CH═CH_2$ | 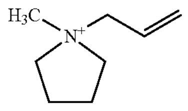 $Cl^-$ |

TABLE 1-continued

| Amine/phosphine employed | Allyl chloride employed | Product |
|---|---|---|
| 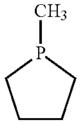 | Cl—CH$_2$—CH═CH$_2$ | 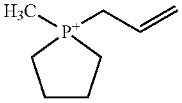 Cl$^-$ |
| 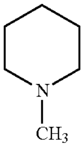 | Cl—CH$_2$—CH═CH$_2$ | 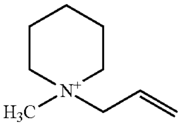 Cl$^-$ |
| 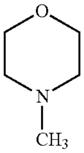 | Cl—CH$_2$—CH═CH$_2$ | 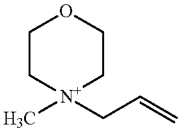 Cl$^-$ |
| 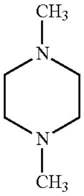 | Cl—CH$_2$—CH═CH$_2$ | 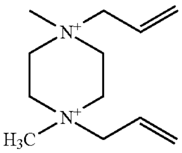 Cl$^-$ |
| 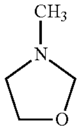 | Cl—CH$_2$—CH═CH$_2$ | 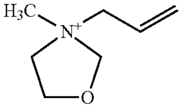 Cl$^-$ |

Example 2

Preparation of Heterocyclic Cations Containing Carboxylate Side Chains or Carbonate Side Chains General Procedure 1 mol of the corresponding amine or phosphine in 300 ml of acetonitrile are initially introduced in a 2 l multinecked round-bottomed flask with precision glass stirrer and brought to 80° C. 1.1 mol of the corresponding halocarboxylate or -carbonate (preferably bromocarboxylate or -carbonate) are subsequently slowly added dropwise over the course of 1.5 h.

The reaction mixture is then allowed to react further at this temperature for 0.5 to 48 hours and stirred into 1 l of ethyl acetate, whereupon the product precipitates as a white solid. The product is filtered off with suction, rinsed with ethyl acetate and dried (rotary evaporator with water bath at about 30° C.). The yield is between 90 and 95%.

TABLE 2

| Amine/ phosphine employed | Chloro(bromo)-alkylcarboxylate | Product |
|---|---|---|
| N(C$_2$H$_5$)$_3$ | Br—CH$_2$—C(O)—O—C$_2$H$_5$ | [N(C$_2$H$_5$)$_3$(CH$_2$—C(O)—O—C$_2$H$_5$)] Br |

TABLE 2-continued

| Amine/ phosphine employed | Chloro(bromo)-alkylcarboxylate | Product |
|---|---|---|
| N(CH$_3$)$_2$(C$_2$H$_5$) | Br—CH$_2$—CH$_2$—C(O)—O—CH$_3$ | [N(CH$_3$)$_2$(C$_2$H$_5$)(CH$_2$—CH$_2$—C(O)—O—CH$_3$)] Br |
| N(CH$_3$)$_2$(C$_2$H$_5$) | Br—CH$_2$—C(O)—CH$_2$—C(O)—O—CH$_3$ | [N(CH$_3$)$_2$(C$_2$H$_5$)(CH$_2$—C(O)—CH$_2$—C(O)—O—CH$_3$)] Br |
| N(CH$_3$)$_2$(C$_2$H$_5$) | Br—CH$_2$—O—C(O)—O—CH$_3$ | [N(CH$_3$)$_2$(C$_2$H$_5$) (CH$_2$—O—C(O)—O—CH$_3$)] Br |
| P(C$_4$H$_9$)$_3$ | Br—CH$_2$—C(O)—O—C$_2$H$_5$ | [P(C$_4$H$_9$)$_3$(CH$_2$—C(O)—O—C$_2$H$_5$)]Br |
| 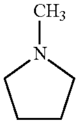 | Br—CH$_2$—CH$_2$—C(O)—O—CH$_3$ | 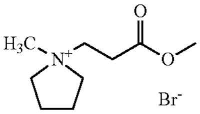 Br$^-$ |
| 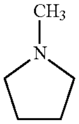 | Br—CH$_2$—C(O)—CH$_2$—C(O)—O—CH$_3$ | 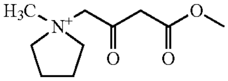 Br$^-$ |
| 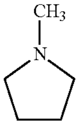 | Br—CH$_2$—O—C(O)—O—CH$_3$ | 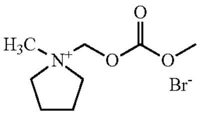 Br$^-$ |
| 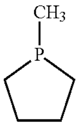 | Br—CH$_2$—CH$_2$—C(O)—O—CH$_3$ | 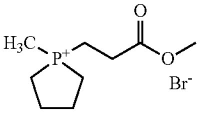 Br$^-$ |
| 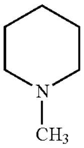 | Br—CH$_2$—CH$_2$—C(O)—O—CH$_3$ | 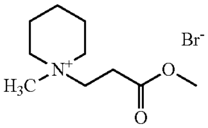 Br$^-$ |
| 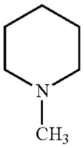 | Cl—CH$_2$—O—C(O)—O—CH$_3$ | 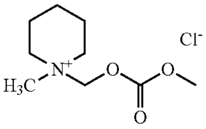 Cl$^-$ |
| 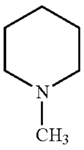 | Cl—CH$_2$—C(O)—CH$_2$—C(O)—O—CH$_3$ | 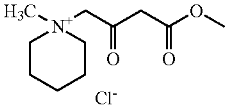 Cl$^-$ |
| 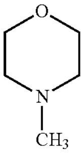 | Cl—CH$_2$—CH$_2$—C(O)—O—CH$_3$ | 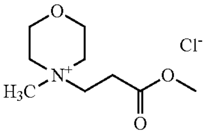 Cl$^-$ |

TABLE 2-continued

| Amine/ phosphine employed | Chloro(bromo)-alkylcarboxylate | Product |
|---|---|---|
| 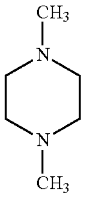 | $Cl—CH_2—CH_2—C(O)—O—CH_3$ | 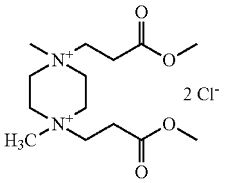 |
| 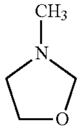 | $Cl—CH_2—CH_2—C(O)—O—CH_3$ | 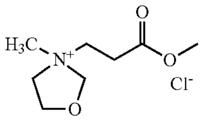 |

Example 3

Preparation of Heterocyclic Cations Containing Cyano-Containing Side Chains

General Procedure 1.1. mol of a chloroalkyl nitrile (or bromo- or iodoalkyl nitrile) are added dropwise to 1 mol of the corresponding amine or phosphine. It must be ensured here that the temperature is held at between 30 and 50°. The reaction mixture is then stirred at 50° C. to 80° C. for 3 h to 48 h (in the case of the formation of solid products, the reaction mixture is diluted with acetonitrile), and the excess chloroalkyl nitrile and solvent is then distilled off in vacuo ($2·10^{-3}$ mbar). The product yield is virtually quantitative.

TABLE 3

| Amine/phosphine employed | Chloroalkyl nitrite | Product |
|---|---|---|
| $N(C_2H_5)_3$ | $Cl—CH_2—CH_2—CN$ | $[N(C_2H_5)_3(CH_2—CH_2—CN)] Cl$ |
| $N(CH_3)_2(C_2H_5)$ | $Cl—CH_2—CH_2—CN$ | $[N(CH_3)_2(C_2H_5) (CH_2—CH_2—CN)] Cl$ |
| $P(C_4H_9)_3$ | $Cl—CH_2—CH_2—CN$ | $[P(C_4H_9)_3(CH_2—CH_2—CN)] Cl$ |
| 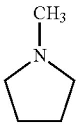 | $Cl—CH_2—CH_2—CN$ | 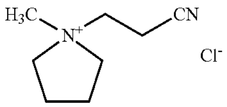 |
| 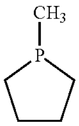 | $Cl—CH_2—CH_2—CN$ | 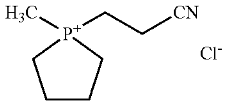 |
| 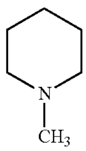 | $Cl—CH_2—CH_2—CN$ | 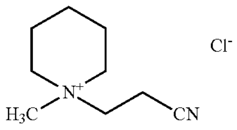 |

TABLE 3-continued

| Amine/phosphine employed | Chloroalkyl nitrite | Product |
|---|---|---|
| 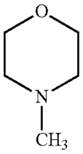 | $Cl—CH_2—CH_2—CN$ | 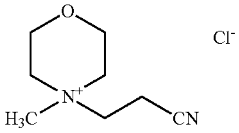 |
| 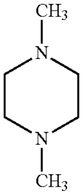 | $Cl—CH_2—CH_2—CN$ | 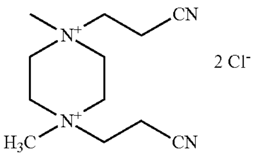 [SMILES: C[N+]1(CCC#N)CC[N+](C)(CCC#N)CC1 ; "2 Cl-"] |
| 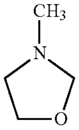 | $Cl—CH_2—CH_2—CN$ | 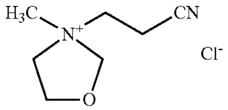 |

Preparation of Fluoroalkylphosphate- and Fluoroalkylphosphinate-Based Reactive Ionic Liquids Example 4

Preparation of Fluoroalkylphosphate-Based Reactive Ionic Liquids

General Procedure 1 mol of the corresponding onium chloride or onium bromide (from the examples described above) are dissolved in 200 ml of deionised water in a flask with magnetic stirrer bar, and 1 mol of the corresponding potassium (or sodium) fluoroalkylphosphate is subsequently added slowly. 2 phases immediately form.

These two phases are stirred at room temperature for a further 1 h. The organic phase is then separated off and washed 5 times with 100 ml of deionised water each time until free from chloride (evidence: 1 molar silver nitrate solution) and dried at 80° C.-90° C. in vacuo.

Example 5.1

Preparation of Bis(Fluoroalkyl)Phosphinate-Based Reactive Ionic Liquids by Means of Phosphoric Acid General Procedure 1 mol of the corresponding onium chloride (from the examples described above) are dissolved in 200 ml of deionised water in a flask with magnetic stirrer bar, and 1 mol of the corresponding bis(fluoroalkyl)phosphinic acid is subsequently added slowly.

The reaction mixture is stirred at room temperature for a further 1 h, and water is distilled off together with hydrochloric acid formed. In order to achieve complete removal of hydrochloric acid, repeated azeotropic distillation with dioxane and water can be used (until a negative test with silver nitrate solution). Drying at 80° C.-90° C. in vacuo gives the bis(fluoroalkyl)phosphinates in virtually quantitative yield.

Example 5.2

Preparation of Bis(Fluoroalkyl)Phosphinate-Based Reactive Ionic Liquids Via the Corresponding Potassium Salts General Procedure 1 mol of the corresponding onium chloride (from the examples described above) is dissolved in isopropanol (or methanol or acetonitrile) in a flask with magnetic stirrer bar, and 1 mol of the corresponding potassium fluoroalkylphosphinate is subsequently added slowly.

The reaction mixture is stirred at room temperature for a further 1 h, and KCl formed is filtered off. Removal of isopropanol (or methanol or acetonitrile) in vacuo with the aid of a rotary evaporator gives the bis(fluoroalkyl)phosphinates in virtually quantitative yield.

Example 5.3

Preparation of Bis(Fluoroalkyl)Phosphinate-Based Reactive Ionic Liquids Via the Corresponding Methylphosphinates 1 to 1.1 mol of the corresponding methyl bis(fluoroalkyl) phosphinate are added to 1 mol of the corresponding onium chloride (or bromide) (from the examples described above) in a flask with magnetic stirrer bar.

The reaction mixture is stirred at room temperature or with heating up to 100° C. for 1 to 20 h, and $CH_3Cl$ (or $CH_3Br$) formed and excess methyl bis(fluoroalkyl)phosphinate are removed in vacuo. Bis(fluoroalkyl)phosphinates form in virtually quantitative yield.

TABLE 4

| Onium salt employed | Potassium salt or phosphinic acid or methyl phosphinate employed | Ionic liquid |
|---|---|---|
| $[N(C_2H_5)_3(CH_2—CH{=}CH_2)]$ Cl | K $F_3P(C_2F_5)_3$ | $[N(C_2H_5)_3(CH_2—CH{=}CH_2)]$ $F_3P(C_2F_5)_3$ |
| $[N(C_2H_5)_3(CH_2—CH{=}CH_2)]$ Cl | K $F_3P(C_4F_9)_3$ | $[N(C_2H_5)_3(CH_2—CH{=}CH_2)]$ $F_3P(C_4F_9)_3$ |

TABLE 4-continued

| Onium salt employed | Potassium salt or phosphinic acid or methyl phosphinate employed | Ionic liquid |
|---|---|---|
| $[N(C_2H_5)_3(CH_2—CH{=}CH_2)]$ Cl | K $OP(O)(C_2F_5)_2$<br>$HOP(O)(C_2F_5)_2$<br>$CH_3OP(O)(C_2F_5)_2$ | $[N(C_2H_5)_3(CH_2—CH{=}CH_2)]$ $OP(O)(C_2F_5)_2$ |
| $[N(C_2H_5)_3(CH_2—CH{=}CH_2)]$ Cl | K $OP(O)(C_4F_9)_2$<br>$HOP(O)(C_4F_9)_2$<br>$CH_3OP(O)(C_4F_9)_2$ | $[N(C_2H_5)_3(CH_2—CH{=}CH_2)]$ $OP(O)(C_4F_9)_2$ |
| $[N(CH_3)(C_2H_5)_3(CH_2—CH{=}CH_2)]$ Cl | K $F_3P(C_2F_5)_3$ | $[N(CH_3)(C_2H_5)_3(CH_2—CH{=}CH_2)]$ $F_3P(C_2F_5)_3$ |
| $[P(C_4H_9)_3(CH_2—CH{=}CH_2)]$ Cl | K $F_3P(C_2F_5)_3$ | $[P(C_4H_9)_3(CH_2—CH{=}CH_2)]$ $F_3P(C_2F_5)_3$ |
| 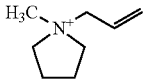 $Cl^-$ | K $F_3P(C_2F_5)_3$ | 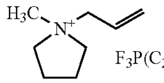 $F_3P(C_2F_5)_3^-$ |
| 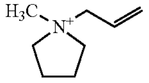 $Cl^-$ | K $F_3P(C_4F_9)_3$ | 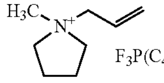 $F_3P(C_4F_9)_3^-$ |
| 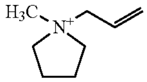 $Cl^-$ | K $OP(O)(C_2F_5)_2$<br>$HOP(O)(C_2F_5)_2$<br>$CH_3OP(O)(C_2F_5)_2$ | 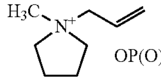 $OP(O)(C_2F_5)_2^-$ |
| 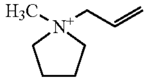 $Cl^-$ | K $OP(O)(C_4F_9)_2$<br>$HOP(O)(C_4F_9)_2$<br>$CH_3OP(O)(C_4F_9)_2$ | 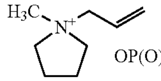 $OP(O)(C_4F_9)_2^-$ |
| 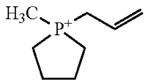 $Cl^-$ | K $F_3P(C_2F_5)_3$ | 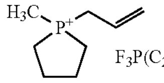 $F_3P(C_2F_5)_3^-$ |
| 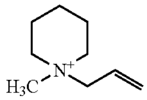 $Cl^-$ | K $F_3P(C_2F_5)_3$ | 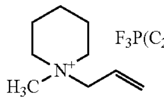 $F_3P(C_2F_5)_3^-$ |
| 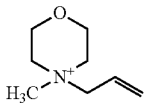 $Cl^-$ | K $F_3P(C_2F_5)_3$ | 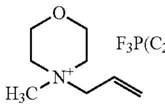 $F_3P(C_2F_5)_3^-$ |

TABLE 5

| Onium salt employed | Potassium salt or methyl phosphinate employed | Ionic liquid |
|---|---|---|
| $[N(C_2H_5)_3(CH_2—C(O)—O—C_2H_5)]$ Br | K $F_3P(C_2F_5)_3$ | $[N(C_2H_5)_3(CH_2—C(O)—O—C_2H_5)]$ $F_3P(C_2F_5)_3$ |
| $[N(C_2H_5)_3(CH_2—C(O)—O—C_2H_5)]$ Br | K $F_3P(C_4F_9)_3$ | $[N(C_2H_5)_3(CH_2—C(O)—O—C_2H_5)]$ $F_3P(C_4F_9)_3$ |
| $[N(C_2H_5)_3(CH_2—C(O)—O—C_2H_5)]$ Br | K $OP(O)(C_2F_5)_2$ | $[N(C_2H_5)_3(CH_2—C(O)—O—C_2H_5)]$ $OP(O)(C_2F_5)_2$ |
| $[N(C_2H_5)_3(CH_2—C(O)—O—C_2H_5)]$ Br | K $OP(O)(C_4F_9)_2$<br>$CH_3OP(O)(C_4F_9)_2$ | $[N(C_2H_5)_3(CH_2—C(O)—O—C_2H_5)]$ $OP(O)(C_4F_9)_2$ |
| $[N(CH_3)_2(C_2H_5)$ $(CH_2—CH_2—C(O)—O—CH_3)]$ Br | K $F_3P(C_2F_5)_3$ | $[N(CH_3)_2(C_2H_5)$ $(CH_2—CH_2\text{-}C(O)\text{-}O\text{-}CH_3)]$ $F_3P(C_2F_5)_3$ |
| $[N(CH_3)_2(C_2H_5)$ $(CH_2—C(O)—CH_2—C(O)—O—CH_3)]$ Br | K $F_3P(C_2F_5)_3$ | $[N(CH_3)_2(C_2H_5)$ $(CH_2—C(O)—CH_2—C(O)—O—CH_3)]$ $F_3P(C_2F_5)_3$ |
| $[N(CH_3)_2(C_2H_5)$ $(CH_2—O—C(O)—O—CH_3)]$ Br | K $F_3P(C_2F_5)_3$ | $[N(CH_3)_2(C_2H_5)$ $(CH_2—O—C(O)—O—CH_3)]$ $F_3P(C_2F_5)_3$ |
| $[P(C_4H_9)_3(CH_2—C(O)—O—C_2H_5)]$ Br | K $F_3P(C_2F_5)_3$ | $[P(C_4H_9)_3(CH_2—C(O)—O—C_2H_5)]$ $F_3P(C_2F_5)_3$ |

TABLE 5-continued
| Onium salt employed | Potassium salt or methyl phosphinate employed | Ionic liquid |
|---|---|---|
| 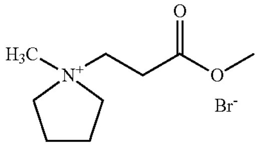 | K $F_3P(C_2F_5)_3$ | 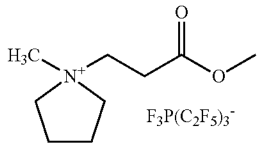 |
| 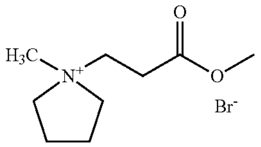 | K $F_3P(C_4F_9)_3$ | 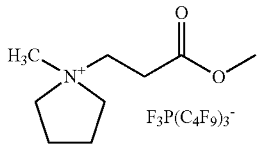 |
| 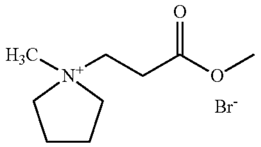 | K $OP(O)(C_2F_5)_2$<br>$CH_3OP(O)(C_2F_5)_2$ | 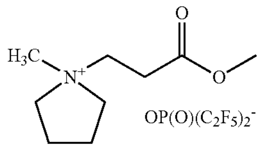 |
| 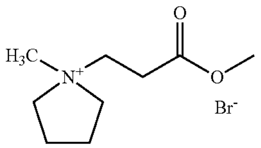 | K $OP(O)(C_4F_9)_2$<br>$CH_3OP(O)(C_4F_9)_2$ | 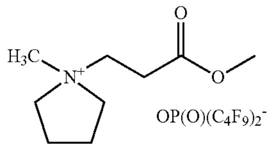 |
| 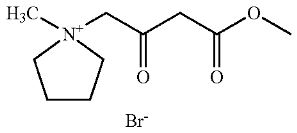 | K $F_3P(C_2F_5)_3$ | 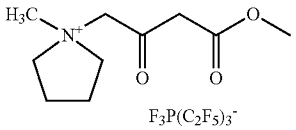 |
| 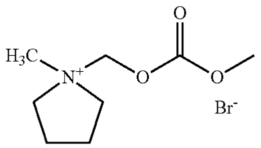 | K $F_3P(C_2F_5)_3$ | 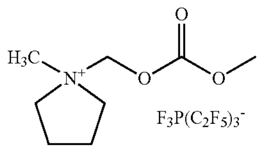 |
| 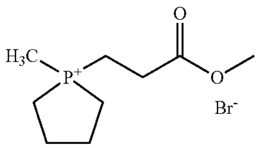 | K $F_3P(C_2F_5)_3$ | 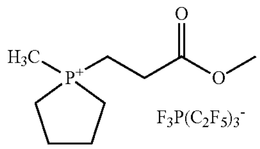 |
| 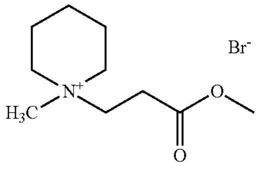 | K $F_3P(C_2F_5)_3$ | 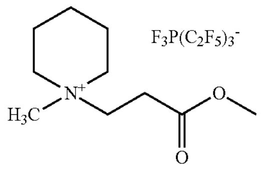 |
| 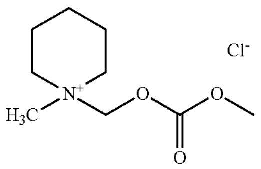 | K $F_3P(C_2F_5)_3$ | 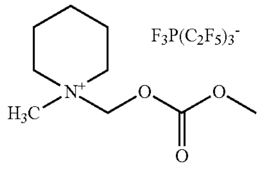 |

TABLE 5-continued

| Onium salt employed | Potassium salt or methyl phosphinate employed | Ionic liquid |
|---|---|---|
| 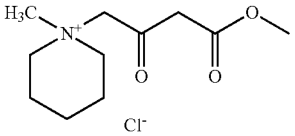 | K $F_3P(C_2F_5)_3$ | 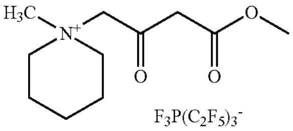 |
| 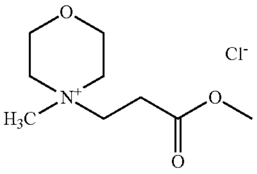 | K $F_3P(C_2F_5)_3$ | 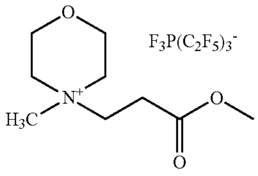 |
| 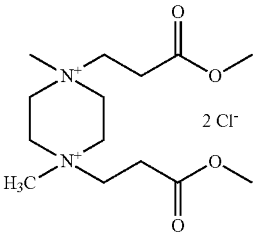 | K $F_3P(C_2F_5)_3$ | 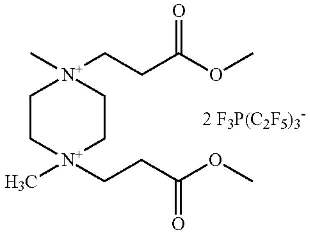 |
| 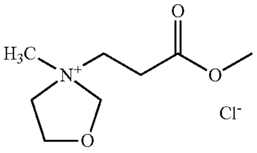 | K $F_3P(C_2F_5)_3$ | 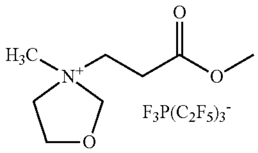 |

TABLE 6

| Onium salt employed | Potassium salt or phosphinic acid or methyl phosphinate employed | Ionic liquid |
|---|---|---|
| $[N(C_2H_5)_3(CH_2—CH_2—CN)]$ Cl | K $F_3P(C_2F_5)_3$ | $[N(C_2H_5)_3(CH_2—CH_2—CN)]$ $F_3P(C_2F_5)_3$ |
| $N(C_2H_5)_3(CH_2—CH_2—CN)]$ Cl | K $F_3P(C_4F_9)_3$ | $N(C_2H_5)_3(CH_2—CH_2—CN)]$ $F_3P(C_4F_9)_3$ |
| $N(C_2H_5)_3(CH_2—CH_2—CN)]$ Cl | K $OP(O)(C_2F_5)_2$<br>$HOP(O)(C_2F_5)_2$<br>$CH_3OP(O)(C_2F_5)_2$ | $N(C_2H_5)_3(CH_2—CH_2—CN)]$ $OP(O)(C_2F_5)_2$ |
| $N(C_2H_5)_3(CH_2—CH_2—CN)]$ Cl | K $OP(O)(C_4F_9)_2$<br>$HOP(O)(C_4F_9)_2$<br>$CH_3OP(O)(C_4F_9)_2$ | $N(C_2H_5)_3(CH_2—CH_2—CN)]$ $OP(O)(C_4F_9)_2$ |
| $[N(CH_3)_2(C_2H_5)$ $(CH_2—CH_2—CN)]$ Cl | K $F_3P(C_2F_5)_3$ | $[N(CH_3)_2(C_2H_5)$ $(CH_2—CH_2—CN)]$ $F_3P(C_2F_5)_3$ |
| $[P(C_4H_9)_3(CH_2—CH_2—CN)]$ Cl | K $F_3P(C_2F_5)_3$ | $[P(C_4H_9)_3(CH_2—CH_2—CN)]$ $F_3P(C_2F_5)_3$ |
| 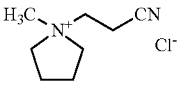 | K $F_3P(C_2F_5)_3$ | 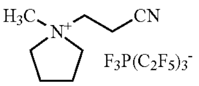 |
| 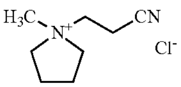 | K $F_3P(C_4F_9)_3$ | 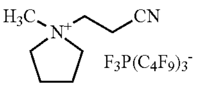 |

TABLE 6-continued

| Onium salt employed | Potassium salt or phosphinic acid or methyl phosphinate employed | Ionic liquid |
|---|---|---|
| 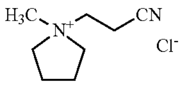 | K $OP(O)(C_2F_5)_2$<br>$HOP(O)(C_2F_5)_2$<br>$CH_3OP(O)(C_2F_5)_2$ | 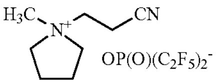 |
| 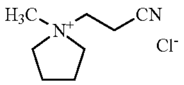 | K $OP(O)(C_4F_9)_2$<br>$HOP(O)(C_4F_9)_2$<br>$CH_3OP(O)(C_4F_9)_2$ | 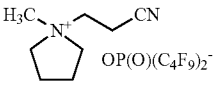 |
| 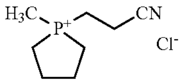 | K $F_3P(C_2F_5)_3$ | 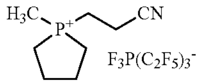 |
| 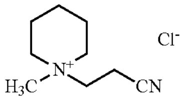 | K $F_3P(C_2F_5)_3$ | 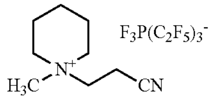 |
| 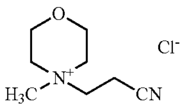 | K $F_3P(C_2F_5)_3$ | 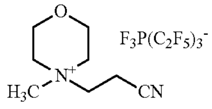 |

TABLE 6-continued

| Onium salt employed | Potassium salt or phosphinic acid or methyl phosphinate employed | Ionic liquid |
|---|---|---|
| 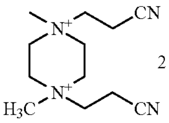 2 Cl⁻ | K $F_3P(C_2F_5)_3$ | 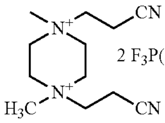 2 $F_3P(C_2F_5)_3^-$ |
| 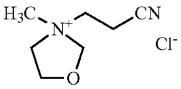 Cl⁻ | K $F_3P(C_2F_5)_3$ | 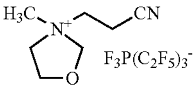 $F_3P(C_2F_5)_3^-$ |

Preparation of Acetate-, Triflate-, Imide- and Methide-Based Reactive Ionic Liquids

Example 5

Preparation of Imide- and Methide-Based Ionic Liquids

General Procedure 1 mol of the corresponding onium chloride or onium bromide (from the examples described above) are dissolved or partially suspended in 200-500 ml of deionised water in a 1 liter flask with magnetic stirrer bar, and 1 mol of the corresponding lithium salt or potassium salt or 1 mol of bis(trifluoromethylsulfonyl)imide (N—H acid) or tris(trifluoromethylsulfonyl)methide (C—H acid) is subsequently added slowly. 2 phases immediately form.

These two phases are stirred at room temperature for a further 1 to 10 hours. The emulsion is then extracted by shaking 3 times with 50 ml of dichloromethane each time. The organic phase is then washed 5 times with 100 ml of deionised water each time until free from chloride (evidence: 1 molar silver nitrate solution).

10 g of $Al_2O_3$ and 1.4 g of activated carbon are added to the organic solution, and the mixture is filtered again after about 1 h and evaporated in a rotary evaporator with a water bath at about 80° C.

TABLE 7

| Onium salt employed | Lithium salt or bis(trifluoro-methylsulfonyl)-imide or tris(tri-fluoromethyl-sulfonyl)methide employed | Ionic liquid |
|---|---|---|
| $[N(C_2H_5)_3(CH_2—CH{=}CH_2)]$ Cl | Li $N(SO_2CF_3)_2$<br>$HN(SO_2CF_3)_2$ | $[N(C_2H_5)_3(CH_2—CH{=}CH_2)]$ $N(SO_2CF_3)_2$ |
| $[N(C_2H_5)_3(CH_2—CH{=}CH_2)]$ Cl | Li $C(SO_2CF_3)_3$<br>$HN(SO_2CF_3)_2$ | $[N(C_2H_5)_3(CH_2—CH{=}CH_2)]$ |
| $[N(CH_3)(C_2H_5)_3(CH_2—CH{=}CH_2)]$ Cl | Li $N(SO_2CF_3)_2$<br>$HN(SO_2CF_3)_2$ | $[N(CH_3)(C_2H_5)_3(CH_2—CH{=}CH_2)]N(SO_2CF_3)_2$ |
| $[P(C_4H_9)_3(CH_2—CH{=}CH_2)]$ Cl | Li $N(SO_2CF_3)_2$<br>$HN(SO_2CF_3)_2$ | $[P(C_4H_9)_3(CH_2—CH{=}CH_2)]$ $N(SO_2CF_3)_2$ |
| 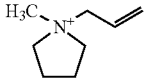 Cl⁻ | Li $N(SO_2CF_3)_2$<br>$HN(SO_2CF_3)_2$ | 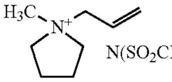 $N(SO_2CF_3)_2^-$ |
| 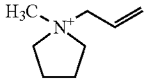 Cl⁻ | Li $C(SO_2CF_3)_3$<br>$HC(SO_2CF_3)_3$ | 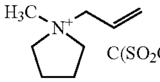 $C(SO_2CF_3)_3^-$ |
| 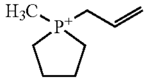 Cl⁻ | Li $N(SO_2CF_3)_2$<br>$HN(SO_2CF_3)_2$ | 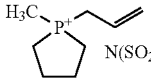 $N(SO_2CF_3)_2^-$ |
| 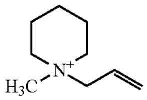 Cl⁻ | Li $N(SO_2CF_3)_2$<br>$HN(SO_2CF_3)_2$ | 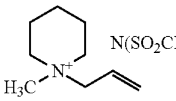 $N(SO_2CF_3)_2^-$ |
| 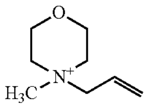 Cl⁻ | Li $N(SO_2CF_3)_2$<br>$HN(SO_2CF_3)_2$ | 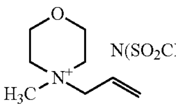 $N(SO_2CF_3)_2^-$ |
| 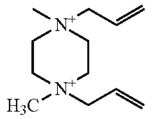 2 Cl⁻ | Li $N(SO_2CF_3)_2$<br>$HN(SO_2CF_3)_2$ | 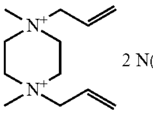 2 $N(SO_2CF_3)_2^-$ |
| 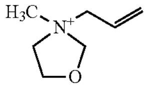 Cl⁻ | Li $N(SO_2CF_3)_2$<br>$HN(SO_2CF_3)_2$ | 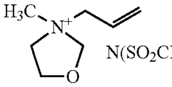 $N(SO_2CF_3)_2^-$ |

TABLE 8

| Onium salt employed | Lithium salt or bis(trifluoro-methylsulfonyl)-imide or tris(tri-fluoromethyl-sulfonyl)methide employed | Ionic liquid |
|---|---|---|
| $[N(C_2H_5)_3(CH_2—C(O)—O—C_2H_5)]$ Br | Li $N(SO_2CF_3)_2$<br>$HN(SO_2CF_3)_2$ | $[N(C_2H_5)_3(CH_2—C(O)—O—C_2H_5)]$ $N(SO_2CF_3)_2$ |
| $[N(C_2H_5)_3(CH_2—C(O)—O—C_2H_5)]$ Cl | Li $OSO_2CF_3$ | $[N(C_2H_5)_3(CH_2—C(O)—O—C_2H_5)]$ $OSO_2CF_3$ |
| $[N(C_2H_5)_3(CH_2—C(O)—O—C_2H_5))$ Cl | Li $OCOCF_3$ | $[N(C_2H_5)_3(CH_2—C(O)—O—C_2H_5)]$ $OCOCF_3$ |

TABLE 8-continued

| Onium salt employed | Lithium salt or bis(trifluoro-methylsulfonyl)-imide or tris(tri-fluoromethyl-sulfonyl)methide employed | Ionic liquid |
|---|---|---|
| $[N(C_2H_5)_3(CH_2—C(O)—O—C_2H_5)]$ Br | Li $C(SO_2CF_3)_3$ $HC(SO_2CF_3)_3$ | $[N(C_2H_5)_3(CH2—C(O)—O—C_2H_5)]$ $C(SO_2CF_3)_3$ |
| $[N(CH_3)_2(C_2H_5)$ $(CH_2—CH_2—C(O)—O—CH_3)]$ Br | Li $N(SO_2CF_3)_2$ $HN(SO_2CF_3)_2$ | $[N(CH_3)_2(C_2H_5)$ $(CH_2—CH_2—C(O)—O\text{-}CH_3)]$ $N(SO_2CF_3)_2$ |
| $[N(CH_3)_2(C_2H_5)$ $(CH_2—C(O)—CH_2—C(O)—O—CH_3)$ Br | Li $N(SO_2CF_3)_2$ $HN(SO_2CF_3)_2$ | $[N(CH_3)_2(C_2H_5)$ $(CH_2—C(O)—CH_2—C(O)—O—CH_3)]$ $N(SO_2CF_3)_2$ |
| $[N(CH_3)_2(C_2H_5)$ $(CH_2—O—C(O)—O—CH_3)]$ Br | Li $N(SO_2CF_3)_2$ $HN(SO_2CF_3)_2$ | $[N(CH_3)_2(C_2H_5)$ $(CH_2—O—C(O)—O—CH_3)]$ $N(SO_2CF_3)_2$ |
| $[P(C_4H_9)_3(CH_2—C(O)—O—C_2H_5)]$ Br | Li $N(SO_2CF_3)_2$ $HN(SO_2CF_3)_2$ | $P(C_4H_9)_3(CH_2—C(O)—O—C_2H_5)]$ $N(SO_2CF_3)_2$ |
| 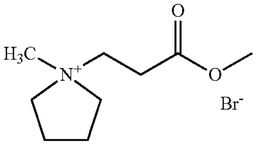 | Li $N(SO_2CF_3)_2$ $HN(SO_2CF_3)_2$ | 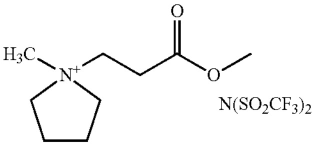 |
| 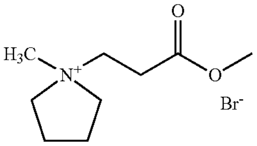 | Li $C(SO_2CF_3)_3$ $HC(SO_2CF_3)_3$ | 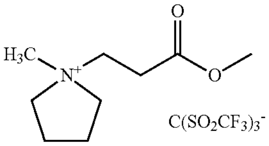 |
| 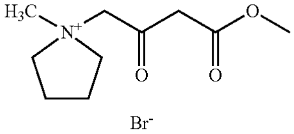 | Li $N(SO_2CF_3)_2$ $HN(SO_2CF_3)_2$ | 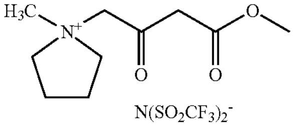 |
| 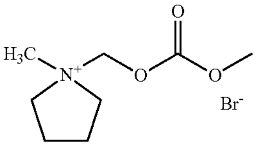 | Li $N(SO_2CF_3)_2$ $HN(SO_2CF_3)_2$ | 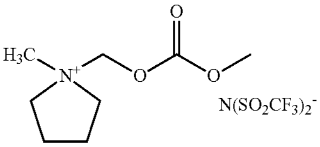 |
| 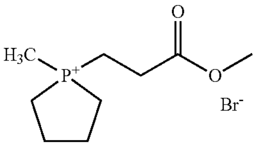 | Li $N(SO_2CF_3)_2$ $HN(SO_2CF_3)_2$ | 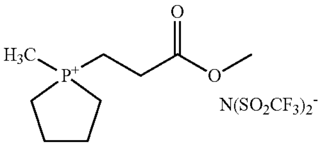 |
| 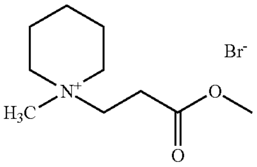 | Li $N(SO_2CF_3)_2$ $HN(SO_2CF_3)_2$ | 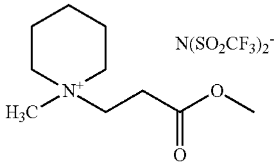 |
| 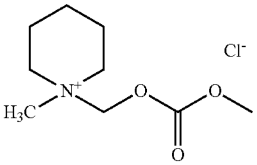 | Li $N(SO_2CF_3)_2$ $HN(SO_2CF_3)_2$ | 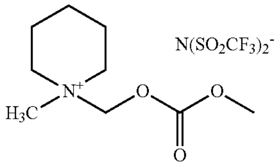 |

TABLE 8-continued

| Onium salt employed | Lithium salt or bis(trifluoromethylsulfonyl)imide or tris(trifluoromethylsulfonyl)methide employed | Ionic liquid |
|---|---|---|
| 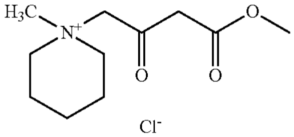 $Cl^-$ | Li $N(SO_2CF_3)_2$<br>$HN(SO_2CF_3)_2$ | 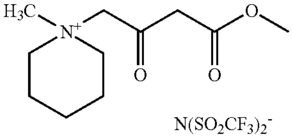 $N(SO_2CF_3)_2^-$ |
| 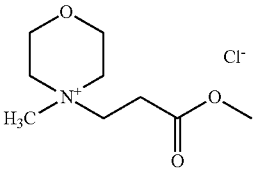 $Cl^-$ | Li $N(SO_2CF_3)_2$<br>$HN(SO_2CF_3)_2$ | 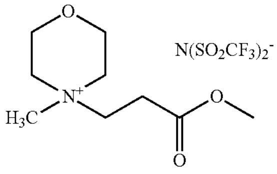 $N(SO_2CF_3)_2^-$ |
| 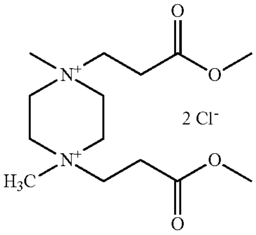 2 $Cl^-$ | Li $N(SO_2CF_3)_2$<br>$HN(SO_2CF_3)_2$ | 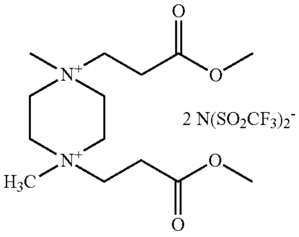 2 $N(SO_2CF_3)_2^-$ |
| 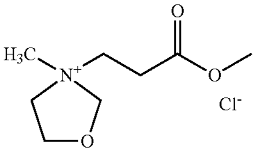 $Cl^-$ | Li $N(SO_2CF_3)_2$<br>$HN(SO_2CF_3)_2$ | 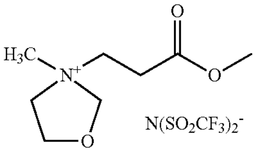 $N(SO_2CF_3)_2^-$ |

TABLE 9

| Onium salt employed | Lithium salt or bis(trifluoromethylsulfonyl)imide or tris(trifluoromethylsulfonyl)methide employed | Ionic liquid |
|---|---|---|
| $[N(C_2H_5)_3(CH_2—CH_2—CN)]$ Cl | Li $N(SO_2CF_3)_2$<br>$HN(SO_2CF_3)_2$ | $[N(C_2H_5)_3(CH_2—CH_2—CN)]$ $N(SO_2CF_3)_2$ |
| $N(C_2H_5)_3(CH_2—CH_2—CN)]$ Cl | Li $C(SO_2CF_3)_3$<br>$HC(SO_2CF_3)_3$ | $N(C_2H_5)_3(CH_2—CH_2—CN)]$ $C(SO_2CF_3)_3$ |
| $[N(CH_3)_2(C_2H_5)$ $(CH_2—CH_2—CN)]$ Cl | Li $N(SO_2CF_3)_2$<br>$HN(SO_2CF_3)_2$ | $[N(CH_3)_2(C_2H_5)$ $(CH_2—CH_2—CN)]$ $N(SO_2CF_3)_2$ |
| $[P(C_4H_9)_3(CH_2—CH_2—CN)]$ Cl | Li $N(SO_2CF_3)_2$<br>$HN(SO_2CF_3)_2$ | $[P(C_4H_9)_3(CH_2—CH_2—CN)]$ $N(SO_2CF_3)_2$ |
| 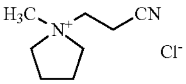 $Cl^-$ | Li $N(SO_2CF_3)_2$<br>$HN(SO_2CF_3)_2$ | 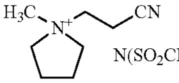 $N(SO_2CF_3)_2^-$ |
| 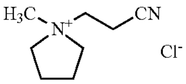 $Cl^-$ | Li $C(SO_2CF_3)_3$<br>$HC(SO_2CF_3)_3$ | 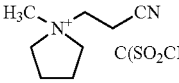 $C(SO_2CF_3)_3^-$ |

TABLE 9-continued

| Onium salt employed | Lithium salt or bis(trifluoromethylsulfonyl)imide or tris(trifluoromethylsulfonyl)methide employed | Ionic liquid |
|---|---|---|
| 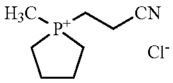 $Cl^-$ | Li $N(SO_2CF_3)_2$<br>$HN(SO_2CF_3)_2$ | 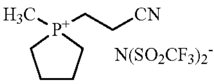 $N(SO_2CF_3)_2^-$ |
| 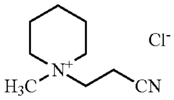 $Cl^-$ | Li $N(SO_2CF_3)_2$<br>$HN(SO_2CF_3)_2$ | 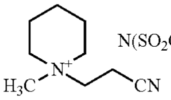 $N(SO_2CF_3)_2^-$ |
| 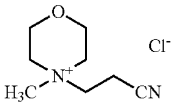 $Cl^-$ | Li $N(SO_2CF_3)_2$<br>$HN(SO_2CF_3)_2$ | 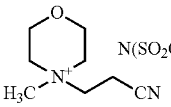 $N(SO_2CF_3)_2^-$ |

TABLE 9-continued

| Onium salt employed | Lithium salt or bis(trifluoro-methyl-sulfonyl)-imide or tris(tri-fluoromethyl-sulfonyl)-methide employed | Ionic liquid |
|---|---|---|
| 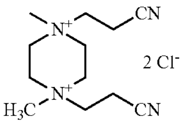 $2\ Cl^-$ | Li $N(SO_2CF_3)_2$ $HN(SO_2CF_3)_2$ | 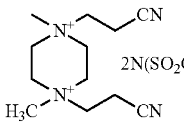 $2N(SO_2CF_3)_2^-$ |
| 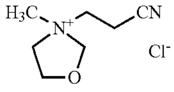 $Cl^-$ | Li $N(SO_2CF_3)_2$ $HN(SO_2CF_3)_2$ | 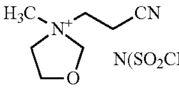 $N(SO_2CF_3)_2^-$ |

Preparation of Trifluoroacetate- or Triflate-Based Ionic Liquids

Example 6.1

Preparation of Triflate-Based Ionic Liquids by Means of Triflic Acid

General Procedure 1 mol of the corresponding onium chloride (from the examples described above) is dissolved in 200-500 ml of deionised water in a flask with magnetic stirrer bar, and 1 mol of triflic acid (=trifluoromethanesulfonic acid) is subsequently added slowly.

The reaction mixture is stirred at room temperature for a further 1 h, and water is distilled off together with HCl formed. In order to achieve complete removal of HCl, repeated azeotropic distillation with dioxane and water can be used (until a negative test with silver nitrate solution). Drying at 80° C.-90° C. in vacuo gives the corresponding triflates in virtually quantitative yield.

Example 6.2

Preparation of Trifluoroacetate- or Triflate-Based Ionic Liquids Via the Corresponding Potassium or Lithium Salts General Procedure 1 mol of the corresponding onium chloride (from the examples described above) is dissolved in isopropanol (or methanol or acetonitrile) in a flask with magnetic stirrer bar, and 1 mol of the corresponding potassium (or lithium) trifluoroacetate or triflate is subsequently added slowly.

The reaction mixture is stirred at room temperature for a further 1 h, and KCl (or LiCl) formed is filtered off. Removal of isopropanol (or methanol or acetonitrile) in vacuo with the aid of a rotary evaporator gives the trifluoroacetates or triflates in virtually quantitative yield.

Example 6.3

Preparation of Trifluoroacetate- and Triflate-Based Ionic Liquids Via the Corresponding Methyl Triflates, Trimethylsilyl Triflates, Triflic Anhydrides or Trifluoroacetic Anhydrides 1 to 1.1 mol of the corresponding methyl triflates or trimethylsilyl triflates or triflic anhydrides or trifluoroacetic anhydrides are added to 1 mol of the corresponding onium chloride (or bromide) (from the examples described above) in a flask with magnetic stirrer bar.

The reaction mixture is stirred at room temperature or with heating up to 100° C. for a further 1 to 48 h, and $CH_3Cl$ (or $CH_3Br$ or $(CH_3)_3SiCl$ or $CF_3SO_2Cl$ or $CF_3COCl$ or $CF_3COBr$) formed and excess methyl or trimethylsilyl triflates or anhydrides are removed in vacuo. Trifluoroacetates or triflates form in virtually quantitative yield.

TABLE 10

| Onium salt employed | Lithium or potassium salt or methyl triflate or anhydride employed | Ionic liquids |
|---|---|---|
| $[N(C_2H_5)_3(CH_2—CH{=}CH_2)]\ Cl$ | K $OSO_2CF_3$, $HOSO_2CF_3$, $CH_3OSO_2CF_3$, $(CH_3)_3SIOSO_2CF_3$, | $[N(C_2H_5)_3(CH_2—CH{=}CH_2)]$ |
| $[N(C_2H_5)_3(CH_2—CH{=}CH_2))\ Cl$ | Li $OCOCF_3$, $(CF_3CO)_2O$ | $[N(C_2H_5)_3(CH_2—CH{=}CH_2)]$ |
| 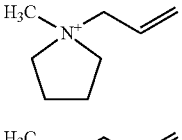 $Cl^-$ | K $OSO_2CF_3$, $HOSO_2CF_3$, $CH_3OSO_2CF_3$, $(CH_3)_3SiOSO_2CF_3$, | 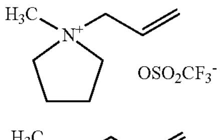 $OSO_2CF_3^-$ |
| 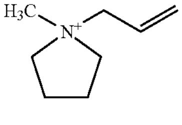 $Cl^-$ | Li $OCOCF_3$, $(CF_3CO)_2O$ | 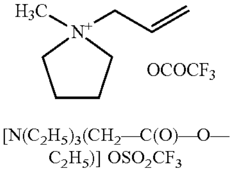 $OCOCF_3$ |
| $[N(C_2H_5)_3(CH_2—C(O)—O—C_2H_5)]\ Br$ | K $OSO_2CF_3$, $HOSO_2CF_3$, $CH_3OSO_2CF_3$, $(CH_3)_3SiOSO_2CF_3$ | $[N(C_2H_5)_3(CH_2—C(O)—O—C_2H_5)]\ OSO_2CF_3$ |
| $[N(C_2H_5)_3(CH_2—C(O)—O—C_2H_5)]\ Br$ | K $OCOCF_3$, $(CF_3CO)_2O$ | $[N(C_2H_5)_3(CH_2—C(O)—O—C_2H_5)]\ OCOCF_3$ |

TABLE 10-continued

| Onium salt employed | Lithium or potassium salt or methyl triflate or anhydride employed | Ionic liquids |
| --- | --- | --- |
| 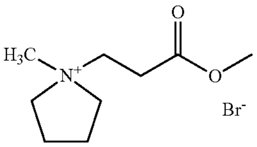 | K $OSO_2CF_3$, $HOSO_2CF_3$, $CH_3OSO_2CF_3$, $(CH_3)_3SiOSO_2CF_3$ | 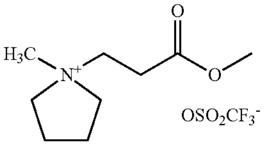 |
| 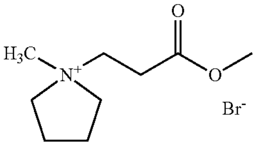 | K $OCOCF_3$, $(CF_3CO)_2O$ | 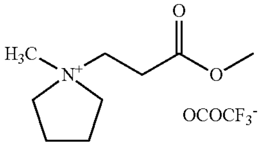 |
| 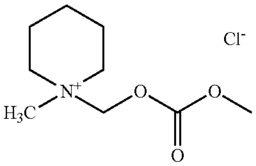 | K $OSO_2CF_3$, $HOSO_2CF_3$, $CH_3OSO_2CF_3$, $(CH_3)_3SIOSO_2CF_3$ | 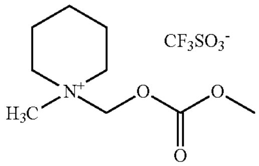 |
| 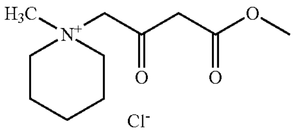 | K $OCOCF_3$, $(CF_3CO)_2O$ | 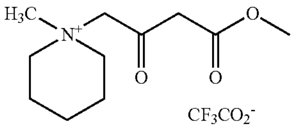 |
| 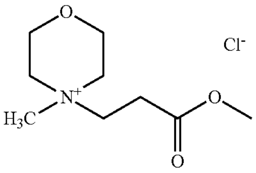 | K $OSO_2CF_3$, $HOSO_2CF_3$, $CH_3OSO_2CF_3$, $(CH_3)_3SiOSO_2CF_3$ | 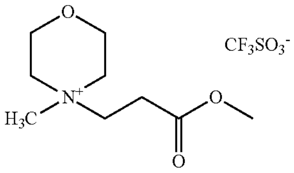 |
| 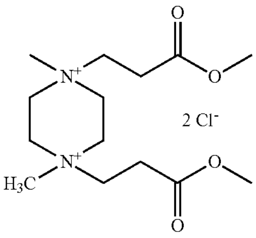 | K $OSO_2CF_3$, $HOSO_2CF_3$, $CH_3OSO_2CF_3$, $(CH_3)_3SiOSO_2CF_3$ | 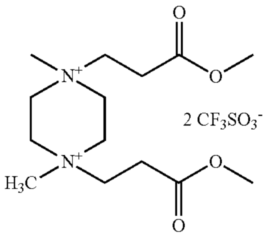 |
| 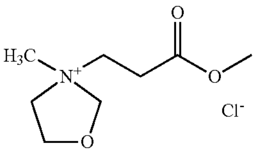 | K $OSO_2CF_3$, $HOSO_2CF_3$, $CH_3OSO_2CF_3$, $(CH_3)_3SiOSO_2CF_3$ | 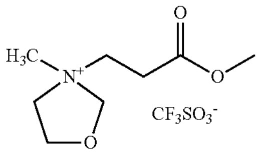 |

TABLE 11

| Onium salt employed | Lithium or potassium salt or methyl triflate or anhydride employed | Ionic liquids |
|---|---|---|
| $N(C_2H_5)_3(CH_2—CH_2—CN)]$ Cl | K $OSO_2CF_3$, $HOSO_2CF_3$, $CH_3OSO_2CF_3$, $(CH_3)_3SiOSO_2CF_3$ | $N(C_2H_5)_3(CH_2—CH_2—CN)]$ $OSO_2CF_3$ |
| $N(C_2H_5)_3(CH_2—CH_2—CN)]$ Cl | K $OCOCF_3$, $(CF_3CO)_2O$ | $N(C_2H_5)_3(CH_2—CH_2—CN)]$ $OCOCF_3$ |
| 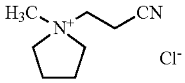 $Cl^-$ | K $OSO_2CF_3$, $HOSO_2CF_3$, $CH_3OSO_2CF_3$, $(CH_3)_3SiOSO_2CF_3$ | 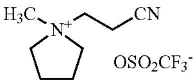 $OSO_2CF_3^-$ |
| 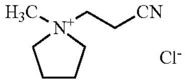 $Cl^-$ | K $OCOCF_3$, $(CF_3CO)_2O$ | 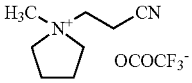 $OCOCF_3^-$ |
| 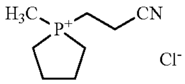 $Cl^-$ | K $OSO_2CF_3$, $CH_3OSO_2CF_3$, $(CH_3)_3SiOSO_2CF_3$ | 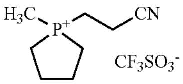 $CF_3SO_3^-$ |
| 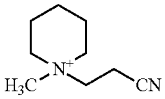 $Cl^-$ | K $OSO_2CF_3$, $HOSO_2CF_3$, $CH_3OSO_2CF_3$, $(CH_3)_3SiOSO_2CF_3$ | 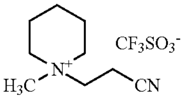 $CF_3SO_3^-$ |
| 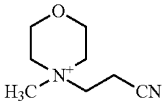 $Cl^-$ | K $OSO_2CF_3$, $HOSO_2CF_3$, $CH_3OSO_2CF_3$, $(CH_3)_3SiOSO_2CF_3$ | 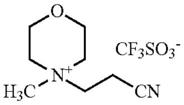 $CF_3SO_3^-$ |

TABLE 11-continued

| Onium salt employed | Lithium or potassium salt or methyl triflate or anhydride employed | Ionic liquids |
|---|---|---|
| 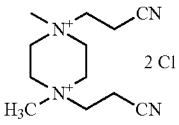 2 Cl | K $OSO_2CF_3$, $HOSO_2CF_3$, $CH_3OSO_2CF_3$, $(CH_3)_3SiOSO_2CF_3$ | 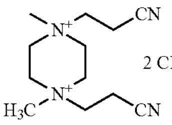 2 $CF_3SO_3^-$ |
| 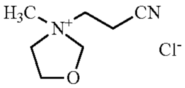 $Cl^-$ | K $OSO_2CF_3$, $HOSO_2CF_3$, $(CH_3)_3SiOSO_2CF_3$ | 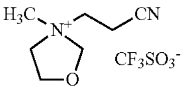 $CF_3SO_3^-$ |

Example 7

Preparation of Borate-, Phosphate- and Aluminate-Based Ionic Liquids

General Procedure 1 mol of the corresponding onium chloride or onium bromide (from the examples described above) is dissolved in 2 l of dichloromethane in a 3 liter flask with magnetic stirrer bar, and 1 mol of the corresponding potassium or lithium salt is subsequently added slowly. After addition, the reaction mixture is stirred for 5 days. 500 nil of deionised water are then added to the batch. 2 phases form. The organic phase is separated off, the aqueous phase is washed with 300 ml of dichloromethane, and all organic phases are combined. The organic phase is washed further twice with 250 nil of deionised water each time and then evaporated to ⅓ and subsequently stirred into 1 l of n-heptane.

Two phases form. The n-heptane phase comprising the ionic liquid is separated off overnight and evaporated in a rotary evaporator with a water bath at 60 to 70° C.

TABLE 12

| Onium salt employed | Potassium or lithium salt employed | Ionic liquid |
|---|---|---|
| $[N(C_2H_5)_3(CH2—CH{=}CH_2)]$ Cl | $K^+$ 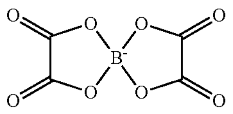 Potassium bisoxalatoborate (KBO | $[N(C_2H_5)_3(CH_2—CH{=}CH_2)]$ BOB |
| $[N(C_2H_5)_3(CH2—CH{=}CH_2)]$ Cl | $K^+$ 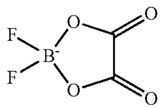 Potassium difluorooxalatoborate (KDFOB) | $[N(C_2H_5)_3(CH_2—CH{=}CH_2)]$ DFOB |
| $[N(C_2H_5)_3(CH2—CH{=}CH_2)]$ Cl | $K^+$ 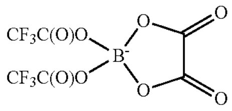 Potassium ditrifluoracetatooxalatoborate (KD(Ac)OB) | $[N(C_2H_5)_3(CH_2—CH{=}CH_2)]$ D(Ac)OB |

TABLE 12-continued

| Onium salt employed | Potassium or lithium salt employed | Ionic liquid |
|---|---|---|
| $[N(C_2H_5)_3(CH2—CH{=}CH_2)]$ Cl | 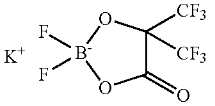 Potassium difluoro(ditrifluoromethyl)-glyconatoborate (KDFGB) | $[N(C_2H_5)_3(CH_2—CH{=}CH_2)]$ DFGB |
| $[N(C_2H_5)_3(CH2—CH{=}CH_2)]$ Cl | 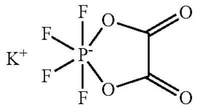 Potassium tetrafluorooxalato-phosphate (KTFOP) | $[N(C_2H_5)_3(CH_2—CH{=}CH_2)]$ TFOP |
| $[N(C_2H_5)_3(CH2—CH{=}CH_2)]$ Cl | 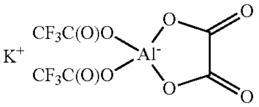 Potassium di(trifluoroacetato) oxalatoaluminate (KD(Ac)OAl) | $[N(C_2H_5)_3(CH_2—CH{=}CH_2)]$ D(Ac)OAl |
| $[N(C_2H_5)_3(CH2—CH{=}CH_2)]$ Cl | 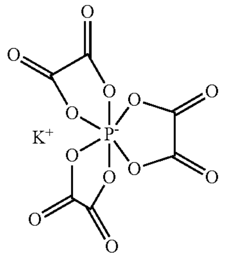 Potassium trisoxalatophosphate (KTOP) | $[N(C_2H_5)_3(CH_2—CH{=}CH_2)]$ TOP |
| $[N(C_2H_5)_3(CH2—CH{=}CH_2)]$ Cl | 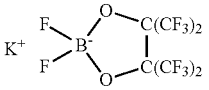 Potassium difluoroperfluoro-pinacolatoborate (KDFPB) | $[N(C_2H_5)_3(CH_2—CH{=}CH_2)]$ DFPB |
| $[N(CH_3)(C_2H_5)_3(CH_2—CH{=}CH_2)]$ Cl | K or Li BOB | $[N(CH_3)(C_2H_5)_3(CH_2—CH{=}CH_2)]$ BOB |
| $[N(CH_3)(C_2H_5)_3(CH_2—CH{=}CH_2)]$ Cl | K or Li DFOB | $[N(CH_3)(C_2H_5)_3(CH_2—CH{=}CH_2)]$ DFOB |
| $[P(C_4H_9)_3(CH_2—CH{=}CH_2)]$ Cl | K or Li BOB | $[P(C_4H_9)_3(CH_2—CH{=}CH_2)]$ BOB |
| $[P(C_4H_9)_3(CH_2—CH{=}CH_2)]$ Cl | K or Li DFOB | $[P(C_4H_9)_3(CH_2—CH{=}CH_2)]$ DFOB |
| 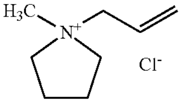 $Cl^-$ | K or Li BOB | 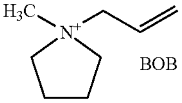 BOB |
| 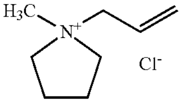 $Cl^-$ | K or Li DFOB | 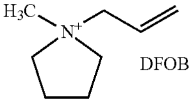 DFOB |

TABLE 12-continued
| Onium salt employed | Potassium or lithium salt employed | Ionic liquid |
|---|---|---|
| 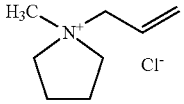 | K or Li TOP | 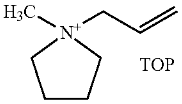 |
| 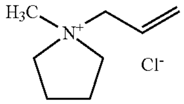 | K or Li TFOP | 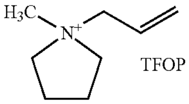 |
| 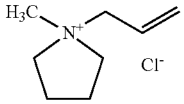 | K or Li D(Ac)OAl | 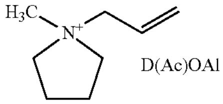 |
| 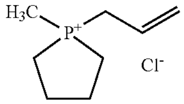 | K or Li BOB | 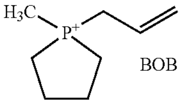 |
| 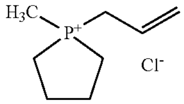 | K or Li DFOB | 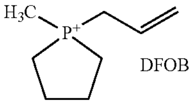 |
| 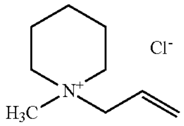 | K or Li BOB | 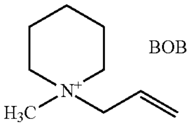 |
| 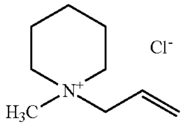 | K or Li DFOB | 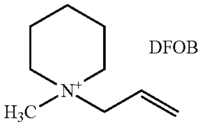 |
| 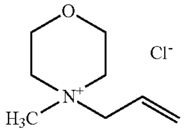 | K or Li BOB | 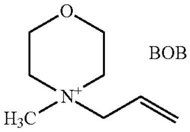 |
| 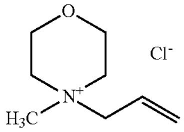 | K or Li DFOB | 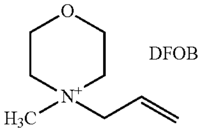 |
| 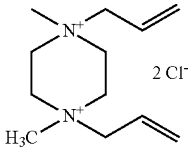 | K or Li BOB | 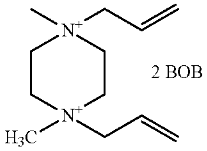 |
| 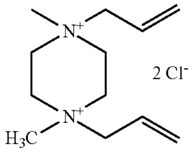 | K or Li DFOB | 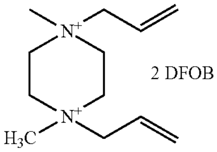 |

TABLE 12-continued

| Onium salt employed | Potassium or lithium salt employed | Ionic liquid |
|---|---|---|
| 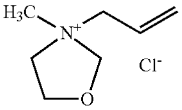 $Cl^-$ | K or Li BOB | 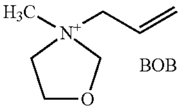 BOB |
| 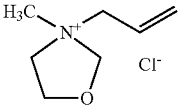 $Cl^-$ | K or Li DFOB | 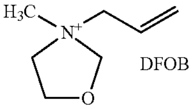 DFOB |

TABLE 13

| Onium salt employed | Potassium or lithium salt employed | Ionic liquid |
|---|---|---|
| $[N(C_2H_5)_3(CH_2—C(O)—O—C_2H_5)]$ Br | K or Li BOB | $[N(C_2H_5)_3(CH_2—C(O)—O—C_2H_5)]$ BOB |
| $[N(C_2H_5)_3(CH_2—C(O)—O—C_2H_5)]$ Br | K or Li DFOB | $[N(C_2H_5)_3(CH_2—C(O)—O—C_2H_5)]$ DFOB |
| $[N(C_2H_5)_3(CH_2—C(O)—O—C_2H_5)]$ Br | K or Li TOP | $[N(C_2H_5)_3(CH_2—C(O)—O—C_2H_5)]$ TOP |
| $[N(C_2H_5)_3(CH_2—C(O)—O—C_2H_5)]$ Br | K or Li D(Ac)OAl | $[N(C_2H_5)_3(CH_2—C(O)—O—C_2H_5)]$ D(Ac)Oal |
| $[N(CH_3)_2(C_2H_5)\ (CH_2—CH_2—C(O)—O—CH_3)]$ Br | K or Li BOB | $[N(CH_3)_2(C_2H_5)\ (CH_2—CH_2—C(O)—O—CH_3)]$ BOB |
| $[N(CH_3)_2(C_2H_5)\ (CH_2—CH_2—C(O)—O—CH_3)]$ Br | K or Li DFOB | $[N(CH_3)_2(C_2H_5)\ (CH_2—CH_2—C(O)—O—CH_3)]$ DFOB |
| $[N(CH_3)_2(C_2H_5)\ (CH_2—C(O)—CH_2—C(O)—O—CH_3)]$ Br | K or Li BOB | $[N(CH_3)_2(C_2H_5)\ (CH_2—C(O)—CH_2—C(O)—O—CH_3)]$ BOB |
| $[N(CH_3)_2(C_2H_5)\ (CH_2—C(O)—CH_2—C(O)—O—CH_3)]$ Br | K or Li DFOB | $[N(CH_3)_2(C_2H_5)\ (CH_2—C(O)—CH_2—C(O)—O—CH_3)]$ BDFOB |
| $[N(CH_3)_2(C_2H_5)\ (CH_2—O—C(O)—O—CH_3)]$ Br | K or Li BOB | $[N(CH_3)_2(C_2H_5)\ (CH_2—O—C(O)—O—CH_3)]$ BOB |
| $[N(CH_3)_2(C_2H_5)\ (CH_2—O—C(O)—O—CH_3)]$ Br | K or Li DFOB | $[N(CH_3)_2(C_2H_5)\ (CH_2—O—C(O)—O—CH_3)]$ DFOB |
| $[P(C_4H_9)_3(CH_2—C(O)—O—C_2H_5)]$ Br | K or Li BOB | $[P(C_4H_9)_3(CH_2—C(O)—O—C_2H_5)]$ BOB |
| $[P(C_4H_9)_3(CH_2—C(O)—O—C_2H_5)]$ Br | K or Li DFOB | $[P(C_4H_9)_3(CH_2—C(O)—O—C_2H_5)]$ DFOB |
| 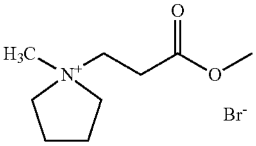 $Br^-$ | K or Li BOB | 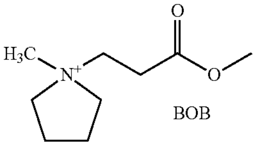 BOB |
| 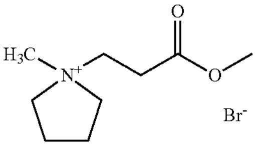 $Br^-$ | K or Li DFOB | 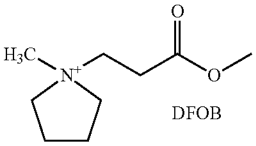 DFOB |
| 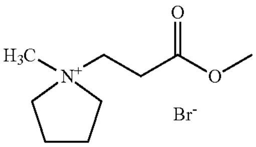 $Br^-$ | K or Li TOP | 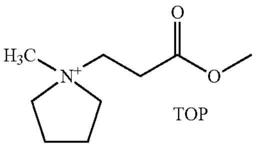 TOP |
| 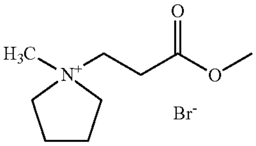 $Br^-$ | K or Li D(Ac)OAl | 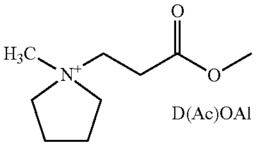 D(Ac)OAl |

TABLE 13-continued
| Onium salt employed | Potassium or lithium salt employed | Ionic liquid |
| --- | --- | --- |
| 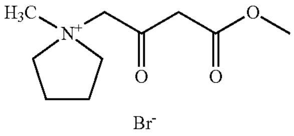 | K or Li BOB | 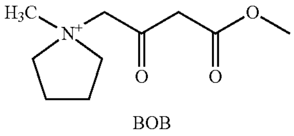 |
| 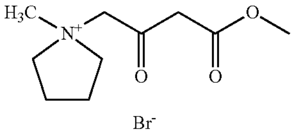 | K or Li DFOB | 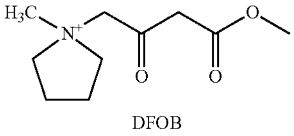 |
| 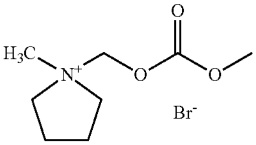 | K or Li BOB | 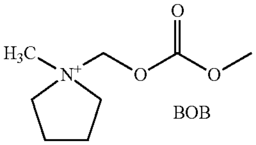 |
| 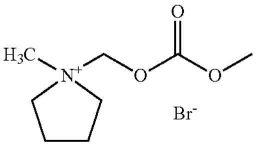 | K or Li DFOB | 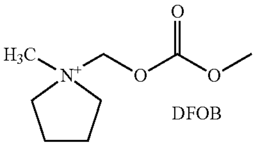 |
| 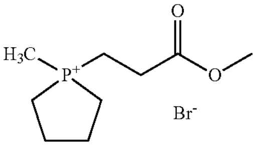 | K or Li BOB | 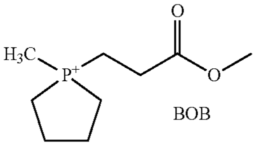 |
| 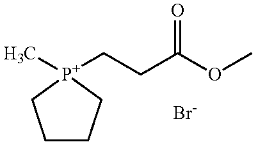 | K or Li DFOB | 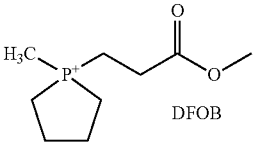 |
| 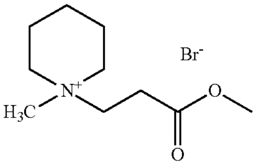 | K or Li BOB | 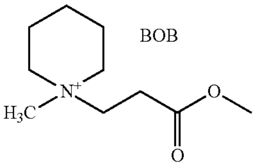 |
| 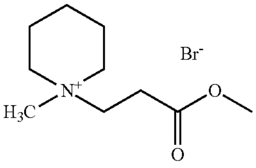 | K or Li DFOB | 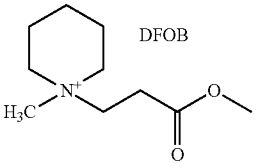 |
| 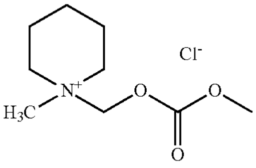 | K or Li BOB | 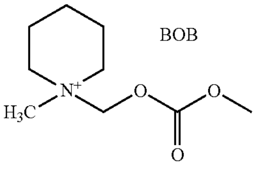 |

TABLE 13-continued
| Onium salt employed | Potassium or lithium salt employed | Ionic liquid |
|---|---|---|
| 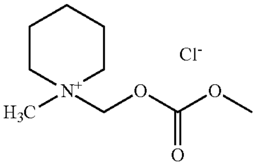 | K or Li DFOB | 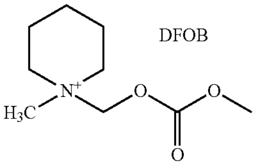 |
| 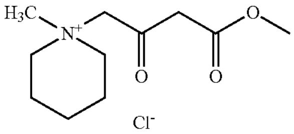 | K or Li BOB | 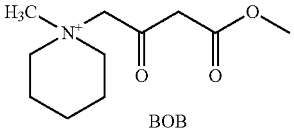 |
| 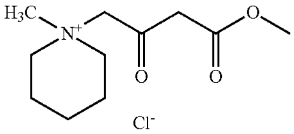 | K or Li DFOB | 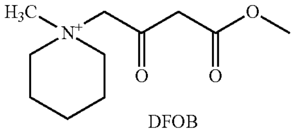 |
| 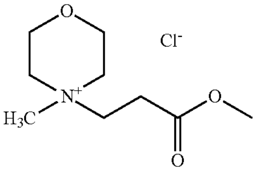 | K or Li BOB | 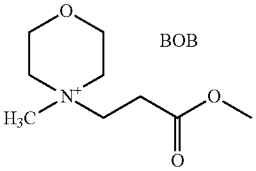 |
| 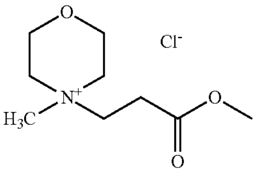 | K or Li DFOB | 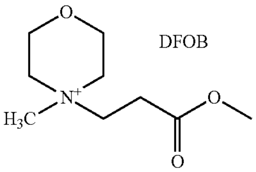 |
| 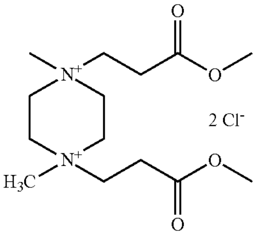 | K or Li BOB | 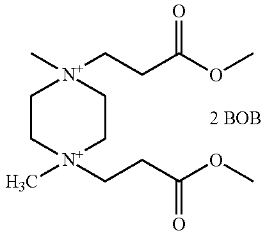 |
| 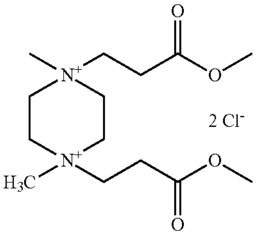 | K or Li DFOB | 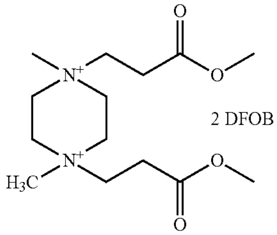 |
| 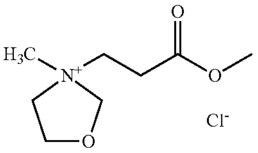 | K or Li BOB | 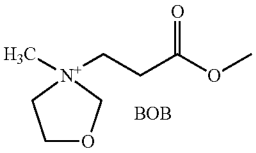 |

TABLE 13-continued

| Onium salt employed | Potassium or lithium salt employed | Ionic liquid |
|---|---|---|
| 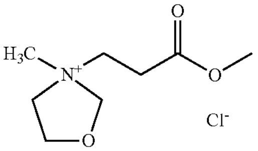 $Cl^-$ | K or Li DFOB | 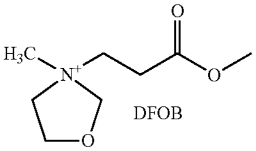 DFOB |

TABLE 14

| Onium salt employed | Lithium or potassium salt or methyl triflate or anhydride employed | Ionic liquid |
|---|---|---|
| N(C2H5)3(CH2—CH2—CN)] Cl | LiBOB or KBOB | N(C2H5)3(CH2—CH2—CN)] BON |
| N(C2H5)3(CH2—CH2—CN)] Cl | K or Li DFOB | N(C2H5)3(CH2—CH2—CN)] DFOB |
| 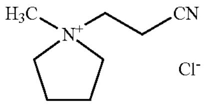 $Cl^-$ | K or Li DFOB | 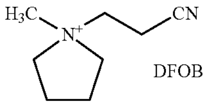 DFOB |
| 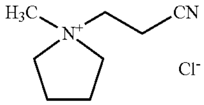 $Cl^-$ | LiBOB or KBOB | 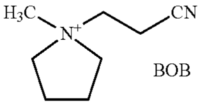 BOB |
| 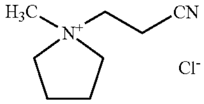 $Cl^-$ | K or LiTOP | 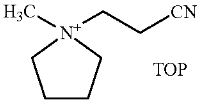 TOP |
| 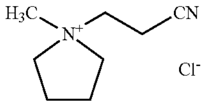 $Cl^-$ | K or Li D(Ac)OAl | 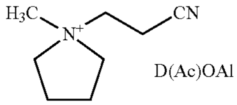 D(Ac)OAl |
| 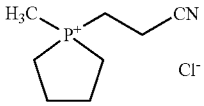 $Cl^-$ | K or Li DFOB | 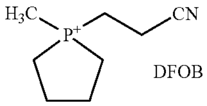 DFOB |
| 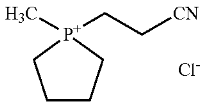 $Cl^-$ | LiBOB or KBOB | 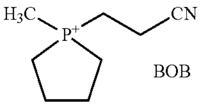 BOB |
| 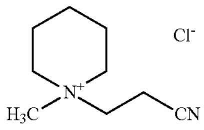 $Cl^-$ | K or Li DFOB | 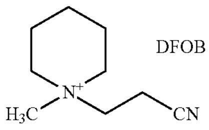 DFOB |
| 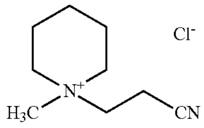 $Cl^-$ | K or Li DFOB | 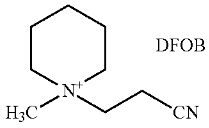 DFOB |

TABLE 14-continued

| Onium salt employed | Lithium or potassium salt or methyl triflate or anhydride employed | Ionic liquid |
|---|---|---|
| 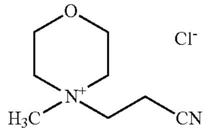 $Cl^-$ | LiBOB or KBOB | 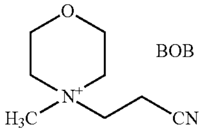 BOB |
| 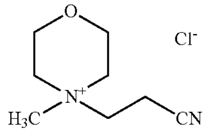 $Cl^-$ | K or Li DFOB | 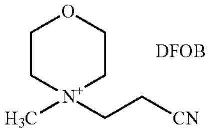 DFOB |
| 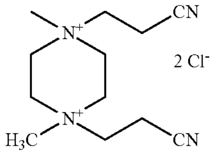 2 $Cl^-$ | K or Li DFOB | 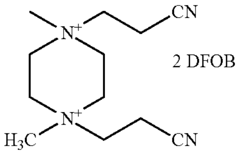 2 DFOB |
| 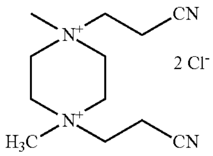 2 $Cl^-$ | LiBOB or KBOB | 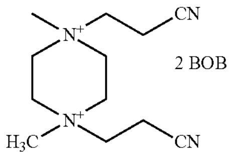 2 BOB |
| 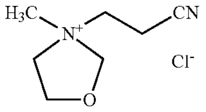 $Cl^-$ | K or Li DFOB | 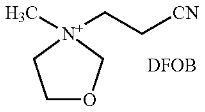 DFOB |
| 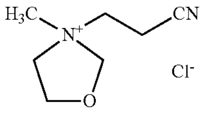 $Cl^-$ | LiBOB or KBOB | 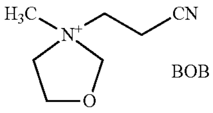 BOB |

Example 8

Investigations on Graphite

In each case, 5 cyclic voltammograms are recorded successively in a measurement cell with graphite anode (SFG 44 with PVDF binder), lithium counterelectrode and lithium reference electrode. To this end, the potential is firstly lowered starting from the rest potential to 0 V against Li/$Li^+$ at a rate of 0.1 mV/s and then returned to the rest potential.

The electrolyte used is 1 M $LiPF_6$ in ethylene carbonate: diethylene carbonate (ratio 3:7) to which about 2% of a reactive ionic liquid selected from Table 7 is added in each case. The reactive ionic liquid forms a passivating top layer at potentials between about 2 V and 0.9 V against $Li/Li^+$ From the second cycle, a 95% yield (±5% measurement tolerance) of the inclusion and extraction of lithium ions in the graphite is achieved. Co-intercalation of the reactive ionic liquid selected from Table 15 in the graphite cannot be observed.

TABLE 15

| Ionic liquid | Yield in % Cycle 1 | Cycle 2 | Cycle 3 | Cycle 4 | Cycle 5 |
|---|---|---|---|---|---|
| Reference* no IL additive | 80 | 82 | 90 | 93 | 95 |
| 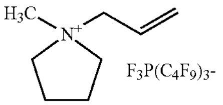 | 75 | 95 | 98 | 99 | 99 |
| 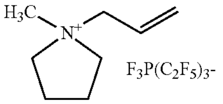 | 76 | 98 | 99 | 99 | 99 |
| 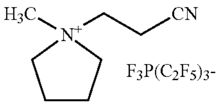 | 72 | 96 | 98 | 98 | 99 |
| 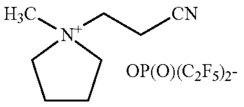 | 70 | 95 | 98 | 99 | 99 |
| 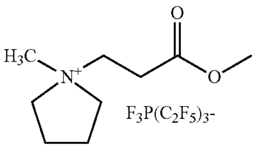 | 77 | 97 | 99 | 99 | 100 |
| 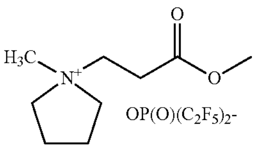 | 72 | 95 | 97 | 98 | 99 |
| 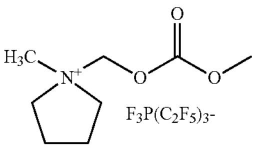 | 78 | 97 | 99 | 99 | 100 |
| 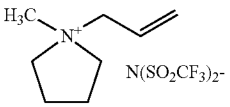 | 75 | 94 | 96 | 99 | 99 |
| 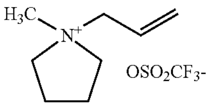 | 72 | 93 | 94 | 97 | 99 |

TABLE 15-continued

| Ionic liquid | Yield in % Cycle 1 | Cycle 2 | Cycle 3 | Cycle 4 | Cycle 5 |
|---|---|---|---|---|---|
| 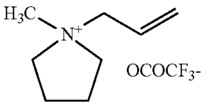 | 74 | 99 | 95 | 99 | 99 |
| 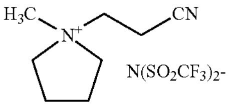 | 74 | 96 | 98 | 98 | 99 |
| 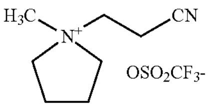 | 72 | 95 | 98 | 99 | 99 |
| 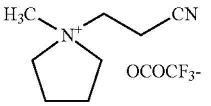 | 72 | 95 | 98 | 99 | 99 |
| 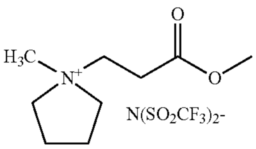 | 77 | 97 | 99 | 99 | 100 |
| 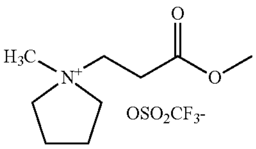 | 72 | 94 | 97 | 98 | 99 |
| 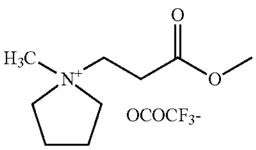 | 72 | 95 | 98 | 98 | 99 |
| 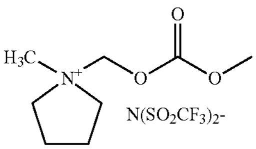 | 80 | 97 | 99 | 99 | 100 |
| 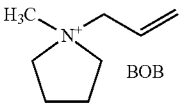 | 75 | 95 | 97 | 99 | 100 |
| 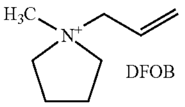 | 72 | 93 | 97 | 98 | 99 |

TABLE 15-continued

| Ionic liquid | Yield in % Cycle 1 | Cycle 2 | Cycle 3 | Cycle 4 | Cycle 5 |
|---|---|---|---|---|---|
| 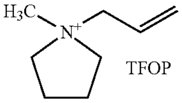 TFOP | 74 | 93 | 95 | 99 | 99 |
| 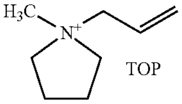 TOP | 74 | 95 | 96 | 99 | 99 |
| 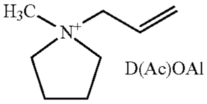 D(Ac)OAl | 72 | 93 | 95 | 98 | 99 |
| 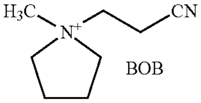 BOB | 74 | 96 | 98 | 98 | 99 |
| 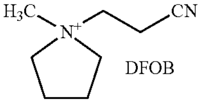 DFOB | 72 | 93 | 96 | 98 | 99 |
| 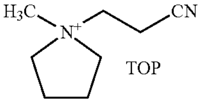 TOP | 72 | 94 | 96 | 98 | 99 |
| 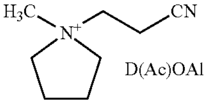 D(Ac)OAl | 72 | 95 | 98 | 99 | 99 |
| 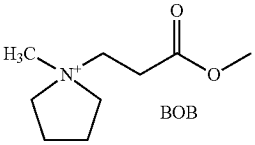 BOB | 77 | 97 | 99 | 100 | 100 |
| 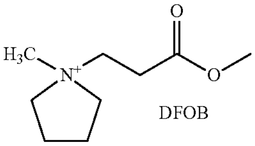 DFOB | 72 | 94 | 97 | 98 | 99 |
| 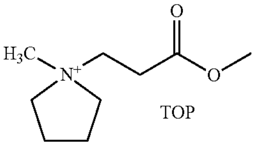 TOP | 72 | 95 | 98 | 98 | 99 |
| 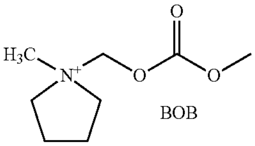 BOB | 80 | 97 | 99 | 100 | 100 |
| 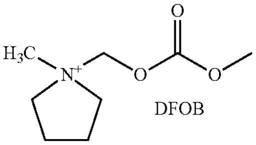 DFOB | 80 | 97 | 99 | 99 | 100 |

*Reference = $LiPF_6$ in EC:DEC (3:7)

Example 9

Investigations on Graphite

In each case, 5 cyclic voltammograms are recorded successively in a measurement cell with graphite anode (SFG 44 with PVDF binder), lithium counterelectrode and lithium reference electrode. To this end, the potential is firstly lowered starting from the rest potential to 0 V against $Li/Li^+$ at a rate of 0.1 mV/s and then returned to the rest potential.

The electrolyte used is 1 M $LiPF_6$ in EC:DEC (3:7) to which about 10% of a reactive ionic liquid selected from Table 8 is added in each case. The reactive ionic liquid forms a passivating top layer at potentials between about 2 V and 0.9 V against $Li/Li^+$. From the second cycle, a greater than 90% yield (±5% measurement tolerance) of the inclusion and extraction of lithium ions in the graphite is achieved.

Co-intercalation of the reactive ionic liquid selected from Table 16 in the graphite cannot be observed.

TABLE 16

| Ionic liquid (IL) | Yield in % Cycle 1 | Cycle 2 | Cycle 3 | Cycle 4 | Cycle 5 |
|---|---|---|---|---|---|
| Reference no IL additive | 80 | 82 | 90 | 93 | 95 |
| 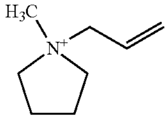 $F_3P(C_4F_9)_3$- | 70 | 93 | 98 | 99 | 99 |
| 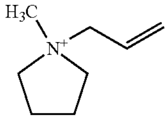 $F_3P(C_2F_5)_3$- | 72 | 96 | 99 | 99 | 99 |
| 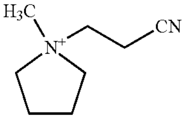 $F_3P(C_2F_5)_3$- | 69 | 90 | 98 | 98 | 99 |

TABLE 16-continued
| | Yield in % | | | | |
|---|---|---|---|---|---|
| Ionic liquid (IL) | Cycle 1 | Cycle 2 | Cycle 3 | Cycle 4 | Cycle 5 |
| 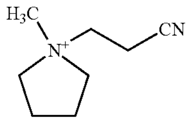 $OP(O)(C_2F_5)_2$- | 69 | 95 | 98 | 99 | 99 |
| 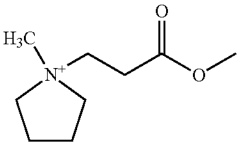 $F_3P(C_2F_5)_3$- | 72 | 97 | 99 | 99 | 100 |
| 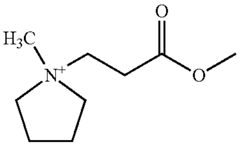 $OP(O)(C_2F_5)_2$- | 70 | 92 | 97 | 98 | 99 |
| 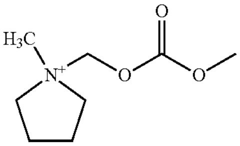 $F_3P(C_2F_5)_3$- | 75 | 95 | 99 | 99 | 100 |
| 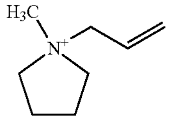 $N(SO_2CF_3)_2$- | 70 | 92 | 95 | 98 | 99 |
| 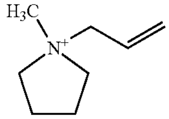 $OSO_2CF_3$- | 69 | 90 | 93 | 97 | 99 |
| 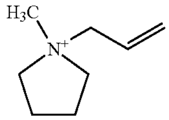 $OCOCF_3$- | 72 | 90 | 95 | 99 | 99 |
| 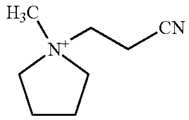 $N(SO_2CF_3)_2$- | 70 | 92 | 97 | 98 | 99 |
| 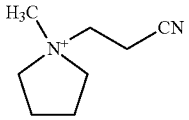 $OSO_2CF_3$- | 72 | 90 | 95 | 99 | 99 |
| 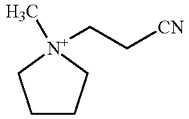 $OCOCF_3$- | 72 | 92 | 98 | 99 | 99 |
| 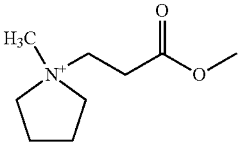 $N(SO_2CF_3)_2$- | 73 | 95 | 99 | 99 | 100 |
| 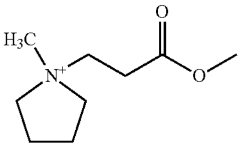 $OSO_2CF_3$- | 70 | 92 | 97 | 98 | 99 |
| 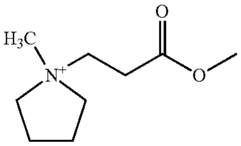 $OCOCF_3$- | 73 | 95 | 98 | 98 | 99 |
| 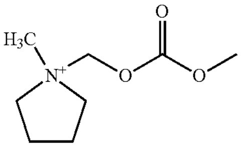 $N(SO_2CF_3)_2$- | 75 | 97 | 99 | 99 | 100 |
| 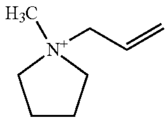 BOB | 70 | 90 | 96 | 98 | 100 |
| 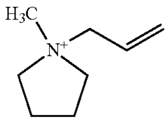 DFOB | 69 | 91 | 96 | 97 | 99 |

TABLE 16-continued

| Ionic liquid (IL) | Yield in % Cycle 1 | Cycle 2 | Cycle 3 | Cycle 4 | Cycle 5 |
|---|---|---|---|---|---|
| 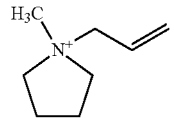 TFOB | 71 | 91 | 95 | 98 | 99 |
| 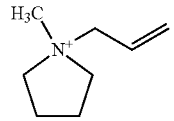 TOP | 72 | 92 | 94 | 99 | 99 |
| 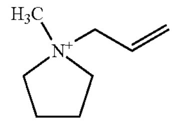 D(Ac)OAl | 70 | 90 | 92 | 97 | 99 |
| 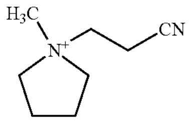 BOB | 71 | 94 | 97 | 98 | 99 |
| 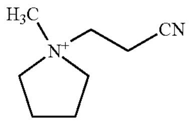 DFOB | 70 | 91 | 94 | 97 | 99 |
| 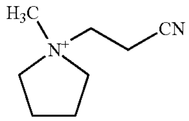 TOP | 69 | 93 | 94 | 98 | 99 |
| 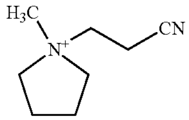 D(Ac)OAl | 69 | 93 | 97 | 98 | 99 |
| 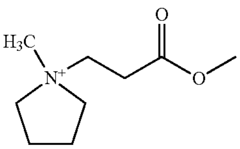 BOB | 75 | 95 | 98 | 198 | 100 |
| 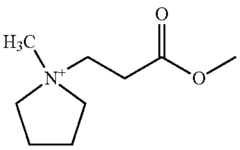 DFOB | 71 | 91 | 97 | 98 | 99 |
| 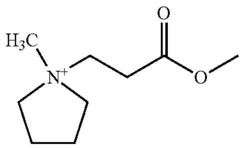 TOP | 70 | 93 | 96 | 98 | 99 |
| 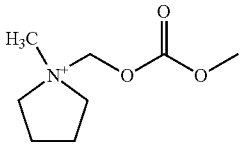 BOB | 78 | 97 | 99 | 100 | 100 |
| 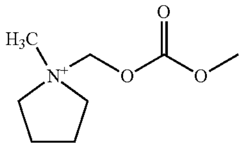 DFOB | 78 | 97 | 99 | 99 | 100 |

* Reference = $LiPF_6$ in EC:DEC (3:7)

Example 10

Investigations of the Oxidation Stability

In each case, 5 cyclic voltammograms are recorded successively in a measurement cell with platinum working electrode, lithium counterelectrode and lithium reference electrode. To this end, the potential is firstly increased starting from the rest potential to 6.0 V against $Li/Li^+$ at a rate of 10 mV/s and then returned to the rest potential.

The electrolyte used is 1 M $LiPF_6$ in EC:DEC (3:7), to which about 2% of a reactive ionic liquid selected from Table 17 is added in each case. The oxidation potential is determined as >5 V against $Li/Li^+$.

A signal below the oxidation stability of the reference electrolyte is not found in any of the systems investigated.

TABLE 17

| | Oxidation stability $E_{ox}$ |
|---|---|
| Reference* no IL additive | >5 V |
| 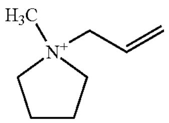 $F_3P(C_4F_9)_3^-$ | >5 V |
| 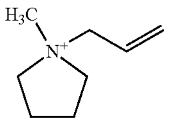 $F_3P(C_2F_5)_3^-$ | >5 V |

TABLE 17-continued
| | Oxidation stability $E_{ox}$ |
|---|---|
| 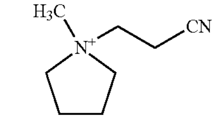 $F_3P(C_2F_5)_3$- | >5 V |
| 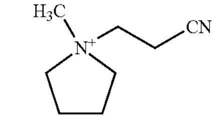 $OP(O)(C_2F_5)_2$- | >5 V |
| 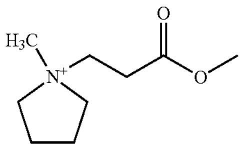 $F_3P(C_2F_5)_3$- | >5 V |
| 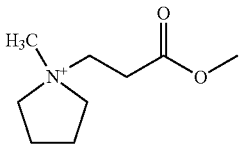 $OP(O)(C_2F_5)_3$- | >5 V |
| 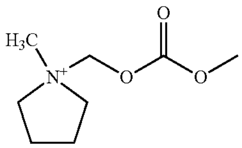 $F_3P(C_2F_5)_2$- | >5 V |
| 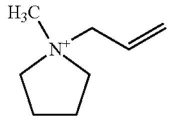 $N(SO_2CF_3)_2$- | >5 V |
| 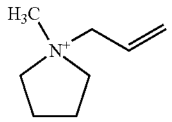 $OSO_2CF_3$- | >5 V |
| 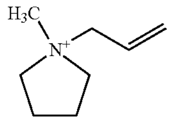 $OCOCF_3$- | >5 V |
| 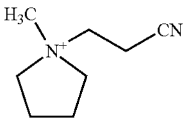 $N(SO_2CF_3)_2$- | >5 V |
TABLE 17-continued
| | Oxidation stability $E_{ox}$ |
|---|---|
| 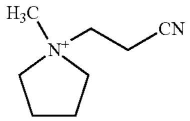 $OSO_2CF_3$- | >5 V |
| 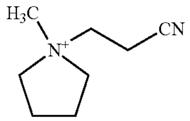 $OCOCF_3$- | >5 V |
| 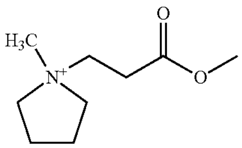 $N(SO_2CF_3)_2$- | >5 V |
| 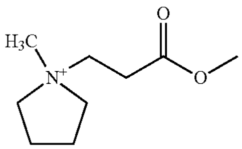 $OSO_2CF_3$- | >5 V |
| 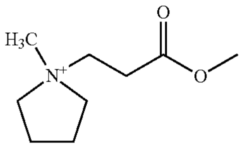 $OCOCF_3$- | >5 V |
| 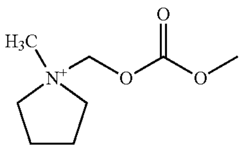 $N(SO_2CF_3)_2$- | >5 V |
| 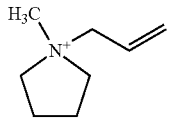 BOB | >5 V |
| 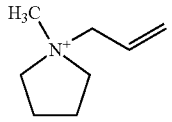 DFOB | >5 V |
| 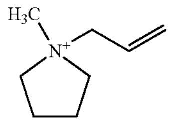 TFOP | >5 V |

TABLE 17-continued

| | Oxidation stability $E_{ox}$ |
|---|---|
| 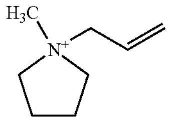 TOP | >5 V |
| 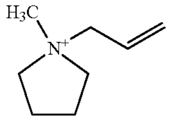 D(Ac)OAl | >5 V |
| 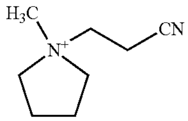 BOB | >5 V |
| 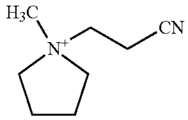 DFOB | >5 V |
| 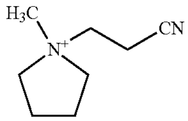 TOP | >5 V |
| 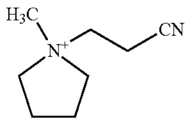 D(Ac)OAl | >5 V |
| 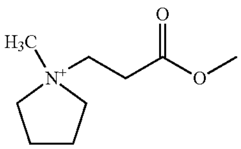 BOB | >5 V |
| 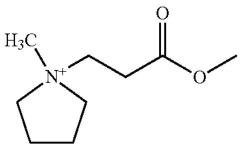 DFOB | >5 V |
| 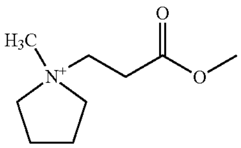 TOP | >5 V |
| 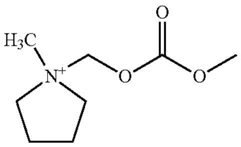 BOB | >5 V |
| 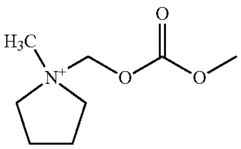 DFOB | >5 V |

*Reference = $LiPF_6$ in EC:DEC (3:7)

Example 11

Investigations of the Oxidation Stability

In each case, 5 cyclic voltammograms are recorded successively in a measurement cell with platinum working electrode, lithium counterelectrode and lithium reference electrode. To this end, the potential is firstly increased starting from the rest potential to 6.0 V against $Li/Li^+$ at a rate of 10 mV/s and then returned to the rest potential.

The electrolyte used is 1 M $LiPF_6$ in EC:DEC to which about 10% of a reactive ionic liquid selected from Table 18 is added in each case. The oxidation potential is determined as >5 V against $Li/Li^+$. A signal below the oxidation stability of the reference electrolyte is not found in any of the systems investigated.

TABLE 18

| Ionic liquid | Oxidation stability $E_{ox}$ |
|---|---|
| Reference* no IL additive | >5 V |
| 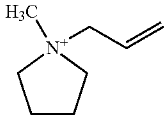 $F_3P(C_4F_9)_3^-$ | >5 V |
| 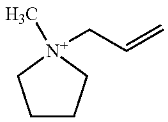 $F_3P(C_2F_5)_3^-$ | >5 V |
| 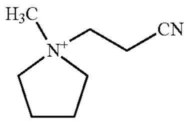 $F_3P(C_2F_5)_3^-$ | >5 V |

TABLE 18-continued
| Ionic liquid | Oxidation stability $E_{ox}$ |
|---|---|
| 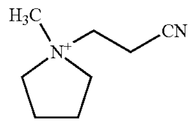 $OP(O)(C_2C_5)_2$- | >5 V |
| 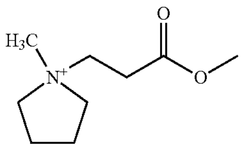 $F_3P(C_2F_5)_3$- | >5 V |
| 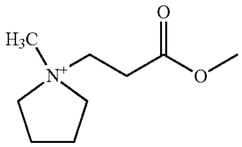 $OP(O)(C_2F_5)_2$- | >5 V |
| 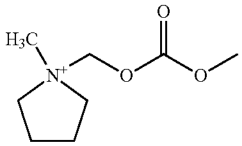 $F_3P(C_2F_5)_3$- | >5 V |
| 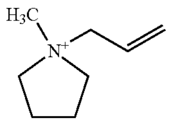 $N(SO_2CF_3)_2$- | >5 V |
| 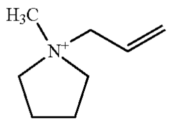 $OSO_2CF_3$- | 4.6-4.8 V |
| 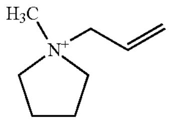 $OCOCF_3$- | 4.5-4.7 V |
| 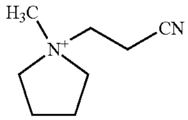 $N(SO_2CF_3)_2$- | >5 V |
| 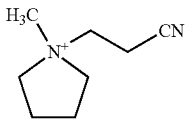 $OSO_2CF_3$- | 4.6-4.8 V |
| 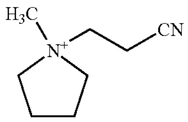 $OCOCF_3$- | 4.7-4.8 V |
| 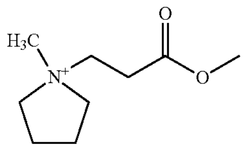 $N(SO_2CF_3)_2$- | >5 V |
| 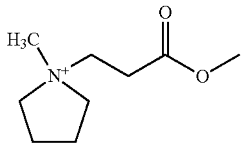 $OSO_2CF_3$- | 4.6-4.8 V |
| 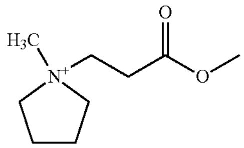 $OCOCF_3$- | 4.5-4.7 V |
| 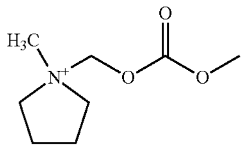 $N(SO_2CF_3)_2$- | >5 V |
| 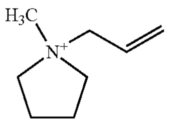 BOB | 4.7-4.8 V |
| 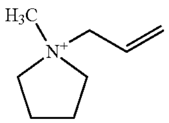 DFOB | 4.8-5.0 V |
| 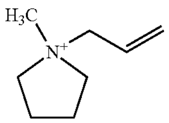 TFOP | 4.8-5.0 V |
| 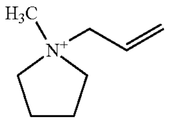 TOP | 4.7-4.8 V |

TABLE 18-continued

| Ionic liquid | Oxidation stability $E_{ox}$ |
|---|---|
| 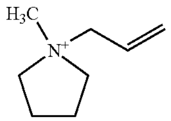 D(Ac)OAl | >5 V |
| 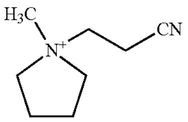 BOB | 4.7-4.8 V |
| 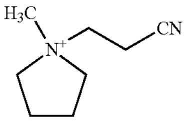 DFOB | 4.8-5.0 V |
| 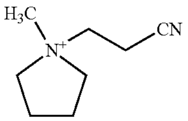 TOP | 4.7-4.8 V |
| 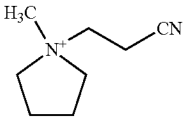 D(Ac)OAl | >5 V |
| 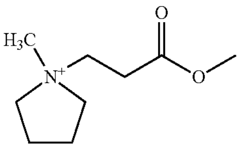 BOB | 4.7-4.8 V |
| 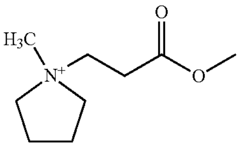 DFOB | 4.8-5.0 V |
| 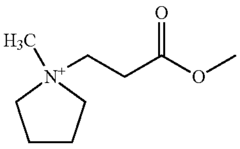 TOP | 4.7-4.8 V |
| 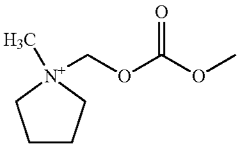 BOB | 4.7-4.8 V |
| 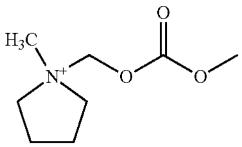 DFOB | 4.8-5.0 V |

*Reference = $LiPF_6$ in EC:DEC (3:7)

The invention claimed is:

1. An ionic liquid of the general formula I $$K^+A^- \quad (I)$$

in which:

$K^+$ denotes a cation of the general formulae IV (IV)

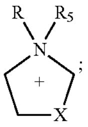

where

X denotes $CH_2$, O, S or NW;

R' denotes $—(CH_2)_n—CN$, $C_1$- to $C_{16}$-alkyl, H;

R denotes $C_1$- to $C_{16}$-alkyl;

$R_5$ denotes $—(CH_2)_N—C(O)—OR$, R" denotes $C_{1-}$ to $C_{16}$-alkyl; where n=2 to 8;

and $A^-$ denotes an anion selected from the group $[F_yP(C_mF_{2m+1})_{6-y}]^-$;

$(C_mF_{2m+1})_2P(O)O^-$;

$(C_mF_{2m+1})P(O)O_2^{2-}$;

$O—C(O)—C_mF_{2m+1}$;

$O—S(O)_2—C_mF_{2m+1}$;

$N(C(O)—C_mF_{2m+1})_2$;

$N(S(O)_2—C_mF_{2m+1})_2$;

$N(C(O)—C_mF_{2m+1})(S(O)_2—C_mF_{2m+1})$;

$N(C(O)—C_mF_{2m+1})(C(O)F)$;

$N(S(O)_2—C_mF_{2m+1})(S(O)_2F)$;

$N(S(O)_2F)_2$;

$C(C(O)—C_mF_{2m+1})_3$;

$C(S(O)_2—C_mF_{2m+1})_3$;

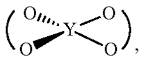, 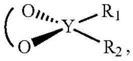, 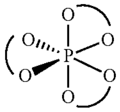, 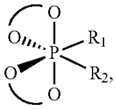, and 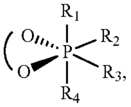, where y=1, 2, 3, 4 or 5 and m=1 to 8, where some of the $CF_2$ groups may be replaced by O, $S(O)_2$, NR or CH), and where

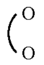

denotes a 1,2- or 1,3-diol, a 1,2- or 1,3-dicarboxylic acid or a 1,2- or 1,3-hydroxycarboxylic acid;

Y denotes B or Al;

$R_1$ to $R_4$ denote halogen, and/or a fluorinated or non-fluorinated alkoxy or carboxyl radical.

2. Electrolyte comprising at least one conductive salt, an aprotic solvent or solvent mixture, at least one ionic liquid according to claim 1 and optionally further additives.

3. Electrolyte according to claim 2, characterized in that the conductive salt is a lithium conductive salt, such as $LiPF_6$, $LiN(SO_2CF_3)_2$, $LiN(SO_2C_2F_5)_2$, $LiF_3P(C_2F_5)_3$, $LiF_3P(C_4F_9)_3$, $LiB(C_2O_4)_2$ or $LiF_2B(C_2O_4)_2$.

4. Electrolyte according to claim 2, characterized in that the conductive salt is selected from the following compounds: $N(C_2H_5)_4BF_4$, $N(C_2H_5)_4PF_6$, $N(C_2H_5)_3(CH_3)BF_4$, $N(C_2H_5)_3(CH_3)PF_6$, $N(C_2H_5)_4N(SO_2CF_3)_2$, $N(C_2H_5)_3(CH_3)N(SO_2CF_3)_2$, $N(C_2H_5)_4F_3P(C_2F_5)_3$, $N(C_2H_5)_3(CH_3)F_3P(C_2F_5)_3$.

5. Electrolyte according to claim 2, characterized in that the aprotic solvent consists of organic open-chain or cyclic carbonates, carboxylic acid esters, nitrites, ethers, lactones or a mixture thereof.

6. A process for the preparation of an ionic liquid of the formula I according to claim 1, comprising the following steps:

Preparation of heterocyclic cations $K^+$ having alkyl-, carboxylate-, carbonate- or cyano-containing side chains according to claim 1 as onium chlorides or bromides from the corresponding amines, phosphines, halocarboxylates, halocarbonates, haloalkyl nitriles or alkyl halides by conventional wet-chemical methods Reaction of these cationic onium chlorides or bromides the corresponding anionic potassium and/or, sodium fluoroalkylphosphates and/or, potassium and/or, sodium bis(fluoroalkyl)phosphinates and/or, potassium and/or, sodium fluoroalkylphosphonates and/or, fluoroalkylphosphoric acids and/or, bis(fluoroalkyl)phosphinic acids and/or, fluoroalkylphosphonic acids and/or, alkyl, in particular methyl, bis(fluoroalkyl) phosphinates or lithium imides or methides and/or, trifluoromethanesulfonic acid or potassium or lithium trifluoroacetates or triflates or alkyl triflates or trimethylsilyl triflates and/or, trifluoromethanesulfonic anhydride or trifluoroacetic anhydride or lithium or potassium borates, phosphates or aluminates in aqueous and/or alcoholic medium or an organic solvent or without a solvent.

7. Electrochemical and/or electro-optical device containing at least one electrolyte which comprises at least one ionic liquid of the general formula I according to claim 1.

8. Electrochemical and/or electro-optical device according to claim 7, characterized in that it is at least one solar cell, lithium ion battery, lithium battery, double-layer capacitor or supercapacitor, lithium capacitor, light-emitting device, electrochemical sensor and/or biosensor.

9. An electrochemical or electro-optical cell comprising an ionic liquid of the formula I according to claim 1.

10. A battery comprising an ionic liquid of the formula I according to claim 1.

11. A secondary lithium battery comprising an ionic liquid of the formula I according to claim 1.

12. A double-layer capacitor or supercapacitor or lithium capacitor comprising an ionic liquid of the formula I according to claim 1.

13. A lithium or lithium ion battery comprising the electrolyte according to claim 2.

14. A double-layer capacitor or supercapacitor or lithium capacitor comprising the electrolyte according to claim 2.

15. The ionic liquid according to claim 1, where X denotes $CH_2$.

16. The ionic liquid according to claim 1, where X denotes $CH_2$ or O.

17. The ionic liquid according to claim 1, where X denotes $CH_2$, O or NR'.

* * * * *